(12) United States Patent
Ramakrishnan

(10) Patent No.: US 8,450,065 B2
(45) Date of Patent: *May 28, 2013

(54) COPY NUMBER VARIATION DETERMINATION, METHODS AND SYSTEMS

(75) Inventor: Ramesh Ramakrishnan, San Jose, CA (US)

(73) Assignee: Fluidigm Corporation, South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/307,817

(22) Filed: Nov. 30, 2011

(65) Prior Publication Data

US 2012/0282604 A1 Nov. 8, 2012

Related U.S. Application Data

(63) Continuation of application No. 12/206,664, filed on Sep. 8, 2008, now Pat. No. 8,148,078.

(60) Provisional application No. 60/967,897, filed on Sep. 7, 2007.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
USPC ................................................ 435/6.12, 91.2
See application file for complete search history.

(56) References Cited

U.S. PATENT DOCUMENTS

| | | | |
|---|---|---|---|
| 4,888,818 A | 12/1989 | Schmitt et al. | |
| 6,143,496 A | 11/2000 | Brown et al. | |
| 6,540,895 B1 | 4/2003 | Spence et al. | |
| 6,605,451 B1 | 8/2003 | Marmaro et al. | |
| 6,753,147 B2 | 6/2004 | Vogelstein et al. | |
| 6,885,982 B2 | 4/2005 | Harris et al. | |
| 6,951,632 B2 | 10/2005 | Unger et al. | |
| 7,042,649 B2 | 5/2006 | Quake et al. | |
| 7,056,660 B1 | 6/2006 | Giesing et al. | |
| 7,059,348 B2 | 6/2006 | Nat | |
| 7,062,418 B2 | 6/2006 | Lee et al. | |
| 7,097,809 B2 | 8/2006 | Van Dam et al. | |
| 7,161,736 B2 | 1/2007 | Legrand et al. | |
| 7,192,629 B2 | 3/2007 | Lammertink et al. | |
| 7,217,367 B2 | 5/2007 | Huang et al. | |
| 7,232,109 B2 | 6/2007 | Driggs et al. | |
| 7,248,413 B2 | 7/2007 | Quake et al. | |
| 7,262,923 B2 | 8/2007 | Quake et al. | |
| 7,279,146 B2 | 10/2007 | Nassef | |
| 7,291,512 B2 | 11/2007 | Unger | |
| 7,368,163 B2 | 5/2008 | Huang et al. | |
| 7,442,556 B2 | 10/2008 | Manger et al. | |
| 7,476,363 B2 | 1/2009 | Unger et al. | |
| 7,526,741 B2 | 4/2009 | Lee et al. | |
| 7,604,965 B2 | 10/2009 | McBride et al. | |
| 7,666,361 B2 | 2/2010 | McBride et al. | |
| 7,678,547 B2 | 3/2010 | Eyal et al. | |
| 7,691,333 B2 | 4/2010 | McBride et al. | |
| 7,749,737 B2 | 7/2010 | McBride et al. | |
| 7,792,345 B2 | 9/2010 | Taylor et al. | |
| 7,815,868 B1 | 10/2010 | Jones et al. | |
| 7,820,427 B2 | 10/2010 | Unger et al. | |
| 7,833,708 B2 | 11/2010 | Enzelberger et al. | |
| 7,837,946 B2 | 11/2010 | McBride et al. | |
| 2002/0012926 A1 | 1/2002 | Quake et al. | |
| 2002/0025529 A1 | 2/2002 | Quake et al. | |
| 2002/0028460 A1 | 3/2002 | Pinkel et al. | |
| 2002/0151040 A1 | 10/2002 | O'Keefe et al. | |
| 2003/0008308 A1 | 1/2003 | Enzelberger et al. | |
| 2004/0180377 A1 | 9/2004 | Manger et al. | |
| 2005/0014175 A1 | 1/2005 | Quake | |
| 2005/0053952 A1 | 3/2005 | Hong et al. | |
| 2005/0072946 A1 | 4/2005 | Studer et al. | |
| 2005/0123947 A1 | 6/2005 | Quake et al. | |
| 2005/0147992 A1 | 7/2005 | Quake et al. | |
| 2005/0196785 A1 | 9/2005 | Quake et al. | |
| 2005/0221373 A1 | 10/2005 | Enzelberger et al. | |
| 2005/0252773 A1 | 11/2005 | McBride | |
| 2006/0019267 A1 | 1/2006 | Quake | |
| 2006/0046258 A1 | 3/2006 | Lapidus et al. | |
| 2006/0054228 A1 | 3/2006 | Unger et al. | |
| 2006/0172408 A1 | 8/2006 | Quake et al. | |
| 2006/0281183 A1 | 12/2006 | Sun et al. | |

(Continued)

FOREIGN PATENT DOCUMENTS

WO WO 01/01025 A2 1/2001
WO WO 2007/092473 A2 8/2007

OTHER PUBLICATIONS

Dube et al., "Mathematical Analysis of Copy Number Variation in a DNA Sample Using Digital PCR on a Nanofluidic Device," PLoS One 3(8):e2876. doi: 10.1371/journal.pone.0002876 (2008).
Iafrate et al., "Detection of large-scale variations in the human genome," Nat Genet, 36:949-951 (2004).
Lupski, "Genomic rearrangements and sporadic diseases," Nat Genet, 39: S43-15 S47 (2007).
Rendon et al., "Global variation in copy number in the human genome," Nature, 444: 444-454 (2006).
Ropers, "New perspectives for the elucidation of genetic disorders," Am J Hum Genet, 81: 199-207 (2007).
Sebat et al., "Large-scale copy number polymorphism in the human 10 genome," Science, 3005: 525-528 (2004).

(Continued)

*Primary Examiner* — Kenneth R. Horlick
*Assistant Examiner* — Joyce Tung
(74) *Attorney, Agent, or Firm* — Kilpatrick Townsend & Stockton LLP

(57) ABSTRACT

The present invention methods and systems for determining copy number variation of a target polynucleotide in a genome of a subject including amplification based techniques. Methods can include pre-amplification of the sample followed by distribution of sample and a plurality of reaction volumes, quantitative detection of a target polynucleotide and a reference polynucleotide, and analysis so as to determine the relative copy number of the target polynucleotide sequence in the genome of the subject.

20 Claims, 8 Drawing Sheets

U.S. PATENT DOCUMENTS

| | | |
|---|---|---|
| 2007/0134807 A1 | 6/2007 | Bao et al. |
| 2007/0224617 A1 | 9/2007 | Quake et al. |
| 2007/0238106 A1 | 10/2007 | Barrett et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |
| 2009/0035838 A1 | 2/2009 | Quake et al. |
| 2009/0069194 A1 | 3/2009 | Ramakrishnan |
| 2009/0142236 A1 | 6/2009 | Unger et al. |
| 2009/0147918 A1 | 6/2009 | Fowler et al. |
| 2009/0239308 A1 | 9/2009 | Dube et al. |
| 2009/0291435 A1 | 11/2009 | Unger et al. |
| 2010/0104477 A1 | 4/2010 | Liu et al. |
| 2010/0120018 A1 | 5/2010 | Quake et al. |
| 2010/0120077 A1 | 5/2010 | Daridon |
| 2010/0138165 A1 | 6/2010 | Fan et al. |
| 2010/0154890 A1 | 6/2010 | Maerkl et al. |
| 2010/0166608 A1 | 7/2010 | Quan et al. |
| 2010/0171954 A1 | 7/2010 | Quake et al. |
| 2010/0183481 A1 | 7/2010 | Facer et al. |
| 2010/0184202 A1 | 7/2010 | McBride et al. |
| 2010/0187105 A1 | 7/2010 | Unger et al. |
| 2010/0196892 A1 | 8/2010 | Quake et al. |
| 2010/0197522 A1 | 8/2010 | Liu et al. |
| 2010/0200782 A1 | 8/2010 | Unger et al. |
| 2010/0230613 A1 | 9/2010 | Pieprzyk et al. |
| 2010/0255471 A1 | 10/2010 | Clarke et al. |
| 2010/0256013 A1 | 10/2010 | Quake et al. |
| 2010/0263732 A1 | 10/2010 | Hansen et al. |
| 2010/0263757 A1 | 10/2010 | Fernandes et al. |
| 2010/0311060 A1 | 12/2010 | Facer et al. |
| 2010/0320364 A1 | 12/2010 | Unger et al. |

OTHER PUBLICATIONS

Unger et al., "Monolithic Microfabricated Valves and Pumps by Mulitlayer Soft Lithography," Science, 288:113-116 (2000).

Volgelstein et al., "Digital PCR," Proc Natl Acad Sci USA, 96: 9236-9241 (1999).

Wong et al., "A comprehensive analysis of common copy-number variations in the human genome," Am J Hum Genet, 80: 91-104 (2007).

Daser et al., "Interrogation of genomes by molecular copy-number counting (MCC)," Nature Methods, Nature Publishing Group, vol. 3, No. 6, Jan. 2006, p. 447-453.

Qin et al., "Studying copy number variations using a nanofluidic platform," Nucleic Acid Research, vol. 36, No. 18, 2008.

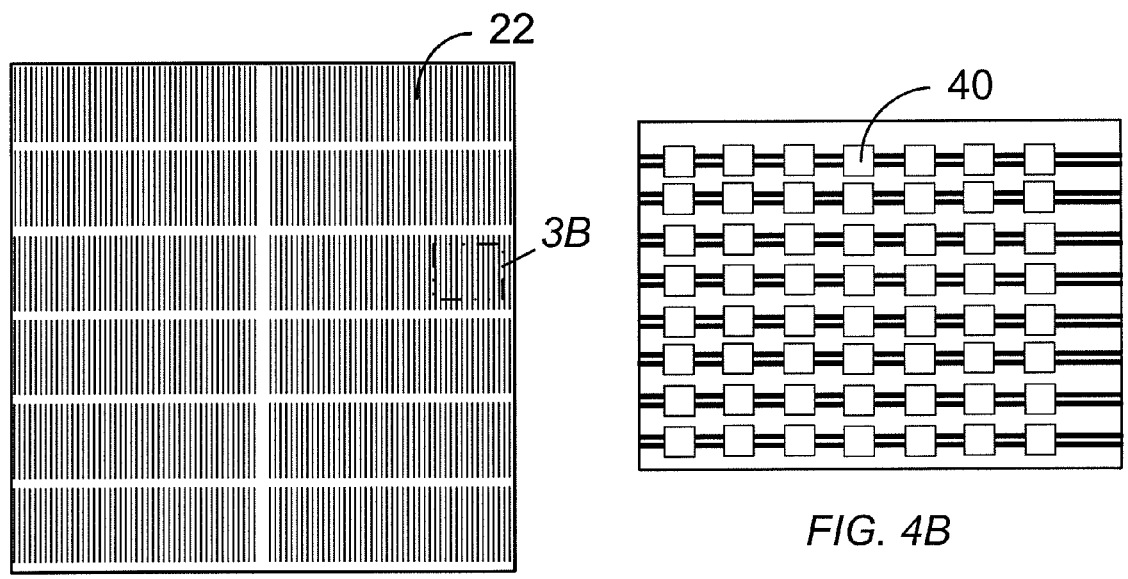
FIG. 4A
FIG. 4B
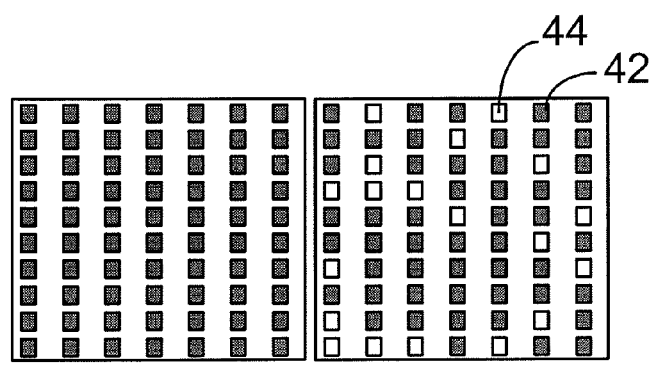
FIG. 4C

| T | T |   |   | T |   | T |   |
|---|---|---|---|---|---|---|---|
| R | T | R |   |   | R |   | T |
|   | T | R |   | T | R |   | T |
| T |   | R |   |   | T |   |   |
|   |   |   |   | T |   | T |   |
| T | R |   | R |   |   | R |   |
|   | R |   |   | T |   | T |   |
| T |   |   | T | T | R |   | R |

*FIG. 8*

COPY NUMBER VARIATION DETERMINATION, METHODS AND SYSTEMS

CROSS-REFERENCE TO RELATED APPLICATIONS

This application claims benefit under 35 U.S.C. §119(e) of U.S. Provisional Patent Application No. 60/967,897, filed Sep. 7, 2007, the full disclosure of which is incorporated herein by reference.

FIELD OF THE INVENTION

The invention relates to a method for determining copy number variation within a genome from small populations or individuals and finds application in biology and medicine.

BACKGROUND OF THE INVENTION

"Digital PCR" refers to a method in which individual nucleic acid molecule present in a sample are distributed to many separate reaction volumes (e.g., chambers or aliquots) prior to PCR amplification of one or more target sequences. The concentration of individual molecules in the sample is adjusted so that after distribution each reaction volume contains fewer than one discrete polynucleotide molecule (or aggregate of linked polynucleotide molecules), and most chambers contain zero or one molecule. Amplification of a target sequence results in a binary digital output in which each chamber is identified as either containing or not containing the PCR product indicative of the presence of the corresponding target sequence. A count of reaction volumes containing detectable levels of PCR end-product is a direct measure of the absolute nucleic acids quantity. In one version of Digital PCR, polynucleotide molecules are distributed by partitioning them into separate reaction volumes. One partition method uses the BioMark™ 12.765 Digital Array (Fluidigm Corp., South San Franscisco, Calif.). This chip utilizes integrated channels and valves that partition mixtures of sample and reagents into 765 nanolitre volume reaction chambers. DNA molecules in each mixture are randomly partitioned into the 765 chambers of each panel. The chip is then thermocycled and imaged on Fluidigm's BioMark real-time PCR system and the positive chambers that originally contained 1 or more molecules can be counted by the digital array analysis software. For discussions of Digital PCR see, for example, Vogelstein and Kinzler, 1999, *Proc Natl Acad Sci USA* 96:9236-41; McBride et al., U.S. Patent Application Publication No. 20050252773, especially Example 5;

Copy number variations (CNVs) are the gains or losses of genomic regions which range from 500 bases on upwards in size (often between five thousand and five million bases). Whole genome studies have revealed the presence of large numbers of CNV regions in human and a broad range of genetic diversity among the general population. CNVs have been the focus of many recent studies because of their roles in human genetic disorders. See, for example Iafrate et al., 2004, Detection of large-scale variation in the human genome. *Nat Genet* 36: 949-951; Sebat et al., 2004, Large-scale copy number polymorphism in the human genome. *Science* 305: 525-528; Redon et al., 2006, Global variation in copy number in the human genome. *Nature* 444: 444-454; Wong et al., 2007, A comprehensive analysis of common copy-number variations in the human genome. *Am J Hum Genet* 80: 91-104; Ropers, 2007, New perspectives for the elucidation of genetic disorders. *Am J Hum Genet* 81: 199-207; Lupski, 2007, Genomic rearrangements and sporadic disease. *Nat Genet* 39: S43-S47, each of which is incorporated by reference. Aneuploidy, such as trisomy or whole chromosome deletion, is a limiting type of copy number variation associated with a variety of human diseases.

BRIEF SUMMARY OF THE INVENTION

The invention relates to a method for determining copy number variation within a genome from small populations or individuals. The method provides for the preamplification of the gene of interest in a sample prior to analysis by digital PCR. The preamplification step allows for the distribution of individual copies of the gene to be distributed into individual PCR reaction samples for detection in a manner that is more representative of actual copy number than when determined by digital PCR without preamplification.

Digital PCR-based methods of the invention have the ability to distinguish less than two-fold differences in gene copy number with great accuracy. For example, it can differentiate between 1, 2, 3 and 4 copies of genes in different samples. In order to ensure that apparent difference in gene copy numbers in different samples are real, and not distorted by differences in sample amounts, we use a term called relative copy number. The relative copy number of a gene (per human genome) can be expressed as the ratio of the copy number of a target gene to the copy number of a single copy reference gene in a DNA sample, which is usually 1. For example, the RNaseP gene is a single-copy gene encoding the RNA moiety for the RNaseP enzyme and may be used as the reference gene in a copy number assay.

A commercially available digital array chip, such as that illustrated in FIG. 3, for performing digital PCR, has been used to quantitate DNA in a sample. The chip has 12 sample input ports for introduction of a sample mixture. Each sample mixture is partitioned into 765 reaction chambers in each of the 12 panels. As is described in the literature (see, e.g., McBride et al., U.S Patent Application Publication No. 20050252773) the ability to quantitate DNA in samples is based on the fact that, when an appropriate quantity of DNA is introduced, single DNA molecules are randomly distributed in the chambers.

By using two assays for two genes (for example RNase P and another gene of interest) with two fluorescent dyes on one chip, it is possible to simultaneously quantitate both RNase P and the other gene in the same DNA sample and obtain a good estimate of the ratio of these two genes and the copy number of the gene of interest.

However, when duplicated, multiple copies of one gene might be closely linked on the same chromosome and therefore can not be partitioned from each other, even on the Digital Array. As a result, multiple copies would behave as one molecule and the total number of copies of the gene would be greatly underestimated.

The present invention addresses this problem by including a preamplification step in the process. Preamplification is a PCR reaction with primers for both the gene of interest and a reference gene (e.g., the RNase P gene). It is typically performed for a limited number of thermal cycles (for example 10 cycles); assuming equal PCR efficiencies, the copy numbers of both genes are proportionally increased in the preamplification step. Using this process, even if multiple copies of a gene are linked together on the genome, after preamplification, each copy of the gene of interest will be amplified separately, and will be partitioned separately into different chambers in the Digital Array. Since the newly generated molecules of both genes reflect the original ratio and they are not linked any more, a digital chip analysis can quantitate the molecules of the two genes and measure the ratio of the two genes (therefore the copy number of the gene of interest) accurately.

Thus, the present invention provides systems and related methods for performing gene-based analyses. More specifically, the methods and systems of the present invention generally relate to determining copy number variation of a polynucleotide of interest in a sample from a subject.

In one aspect the invention provides a method for determining the relative copy number of a target polynucleotide sequence in a genome of a subject, including the steps of:

a) pre-amplifying a target gene sequence and a reference gene sequence in a sample containing genomic DNA of the subject; thereby producing an amplified sample;

b) carrying out digital PCR by distributing product of (a) into a plurality of isolated reaction volumes, amplifying target and reference gene sequences in each reaction volume, and determining the relative quantity of target and reference gene sequences in the amplified sample, where the relative quantity of the target and reference gene sequences in the amplified sample correspond to relative quantity of the target and reference gene sequences in the genome.

In a related aspect the invention provides a method for determining the relative copy number of a target polynucleotide sequence in a genome of a subject, including the steps of:

pre-amplifying a target gene sequence and a reference gene sequence in a sample containing genomic DNA of the subject;

assaying the target gene sequence and the reference gene sequence of the preamplified sample by digital PCR;

determining (a) the number of amplified polynucleotide molecules containing the target gene sequence and (b) the number of amplified polynucleotide molecules containing the reference gene sequence and determining the ratio of (a) to (b).

In a related aspect the invention provides a method for determining a copy number of a target polynucleotide sequence in a genome of a subject, including the steps of:

conducting a first polynucleotide amplification of a DNA sample obtained from a subject, wherein both a target polynucleotide sequence and a reference polynucleotide sequence, said reference sequence having a predetermined genomic copy number N, are amplified, thereby producing an amplified sample;

distributing all or a portion of the amplified sample into a plurality of isolated reaction volumes;

in each reaction volume conducting a second polynucleotide amplification in which the target polynucleotide sequence or a subsequence thereof is amplified if present and the reference polynucleotide sequence or a subsequent thereof is amplified if present;

determining the number of reaction volumes in which the target polynucleotide sequence or subsequence thereof is present A and determining (b) the number of reaction volumes in which the reference polynucleotide sequence or subsequence thereof is present B; where the copy number of the target polynucleotide in the genome is approximately equal to (A)/(B)×N.

In some embodiments the sample is from a human. In particular embodiments the ratio of (a) to (b) is about 0.5 and there is a deletion of (a) on one chromosome, or the ratio of (a) to (b) is about 1.5 and there is a duplication of (a) on one chromosome. In some embodiments a ratio of target gene sequence to reference gene sequence substantially deviating from a value of 1 indicates an abnormal target gene sequence copy number in the genome of the patient.

In some embodiments conducting the first polynucleotide amplification includes combining the biological sample with a composition comprising primers specific for the target polynucleotide sequence and primers specific for reference polynucleotide sequence, and conducting a polymerase chain reaction (PCR) assay so as to separately amplify target polynucleotide and reference polynucleotide in substantially equal proportion.

In some embodiments the first polynucleotide amplification has from 4 to 15 thermocycles. In some embodiments the reaction volumes are disposed in a microfluidic device, and the first polynucleotide amplification is conducted in a reaction volume separate from the microfluidic device.

In some embodiments prior to the step of distributing, all or a portion of the amplified sample is combined with reagents selected for amplification of target gene sequence and reference gene sequence. Usually a portion is used, and the amplified sample may be diluted prior to distribution of a portion to the reaction volumes. In some embodiments the amplification is PCR amplification.

In some embodiments the reference gene sequence amplification primers used in the first polynucleotide amplification step are the same as those used in the second polynucleotide amplification step. In some embodiments the target gene sequence amplification primers used in the first polynucleotide amplification step are the same as those used in the second polynucleotide amplification step. In some embodiments the reagents comprise a first probe that selectively hybridizes to a target gene sequence and a second probe that selectively hybridizes to a reference gene sequence under conditions suitable for polynucleotide amplification. In some embodiments the first and second probes comprise different detectable labels, and wherein binding of the first or second probe or degradation of the first or second probe upon polymerase chain reaction (PCR) based polymerization results in a change in detectable fluorescence of the respective detectable label.

In some embodiments the reference gene sequence comprises a polynucleotide sequence at least partially encoding an RNaseP enzyme, beta-actin or GAPDH. In some embodiments, determining the relative copy number of the target gene sequence comprises detecting a loss of heterozygosity in the genome of the subject. In some embodiments a ratio of target gene sequence to reference gene sequence with a value substantially greater than or less than 1 indicates a loss of heterozygosity in the genome of the patient.

For a fuller understanding of the nature and advantages of the present invention, reference should be had to the ensuing detailed description taken in conjunction with the accompanying drawings. The drawings represent embodiments of the present invention by way of illustration. The invention is capable of modification in various respects without departing from the invention. Accordingly, the drawings/figures and description of these embodiments are illustrative in nature, and not restrictive.

BRIEF DESCRIPTION OF THE DRAWINGS

FIGS. 4A-4C depict portions of the microfluidic device illustrated, for example, in FIG. 1.

FIG. 8 is a schematic showing the partial results of an imaginary experiment in which the copy number of target sequence T is determined. A 64×64 matrix of reaction volumes is illustrated in which a target sequence was amplified and detected using VIC labeled (yellow) probes and a single copy reference sequence were amplified and detected using FAM labeled (green) probes. 19 reaction volumes with yellow-labels and 12 reaction volumes with green-labels are detected, indicating a ratio of approximately 1.5 (19/12=1.58≈1.5) indicating there are three copies of the target sequence per diploid genome.

DETAILED DESCRIPTION OF THE INVENTION

Figure 1:
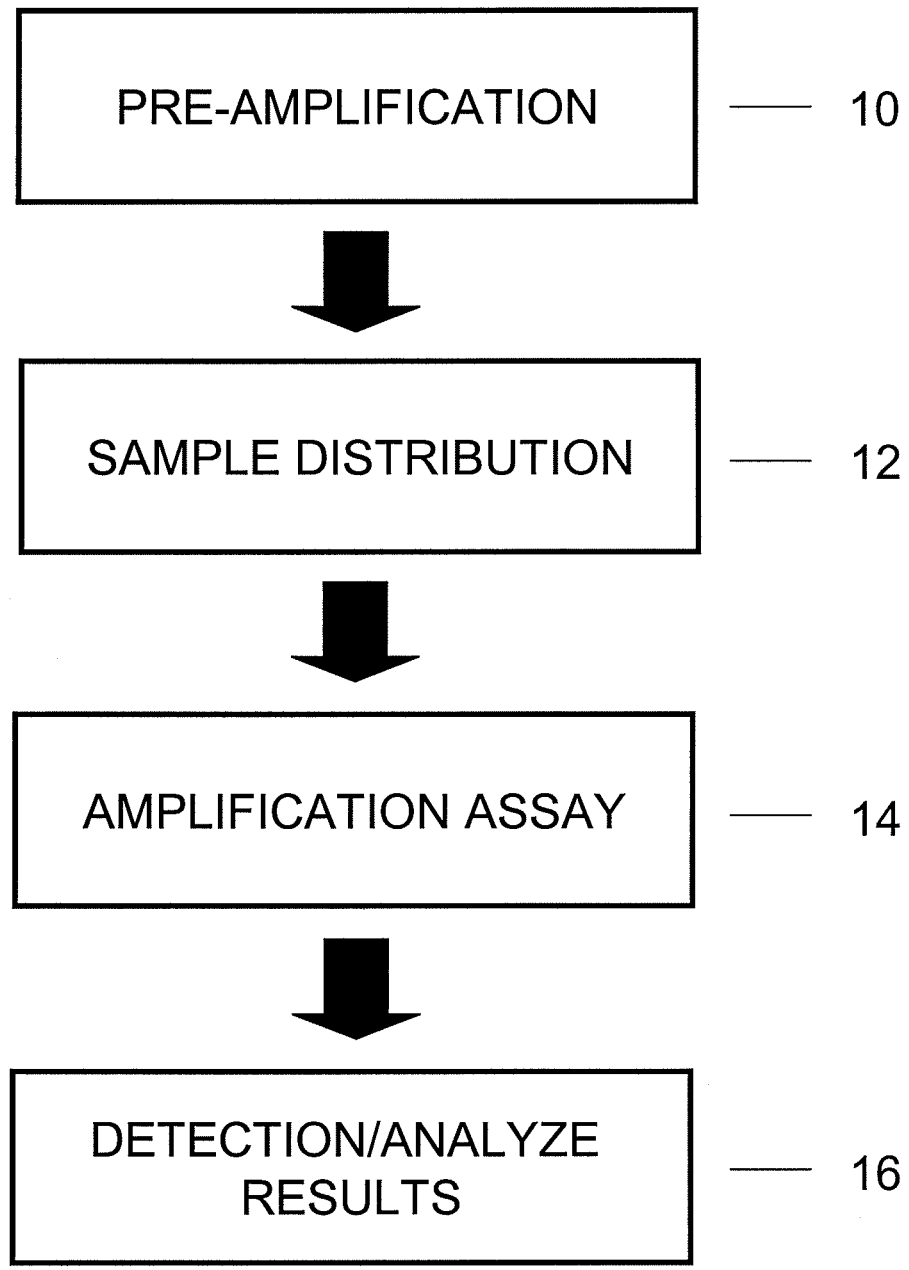
FIG. 1 is a flow chart illustrating general steps of an inventive method as described herein.

The present invention methods and systems for determining copy number of a target polynucleotide sequence in a genome of a patient, including variations in copy number associated with genetic diseases. In particular, methods and systems described herein can be used to detect copy number variation of a target polynucleotide in the genome of a patient using genomic material present within a sample derived from the patient. Techniques of the present invention will typically employ polynucleotide amplification based assays to determine the relative number of copies of a target polynucleotide sequence and a reference polynucleotide sequence in a sample. The genomic copy number is known for the reference sequence. As such, target polynucleotide copy number can be analyzed relative to the reference polynucleotide so as to determine the relative copy number of the target polynucleotide. The target and/or reference polynucleotide sequences are sometimes referred to as "genes." However, it will be appreciated the term "gene" does not indicate the sequence necessarily encodes a protein (or RNA).

Copy number detection and analysis techniques can make use of certain high-throughput devices suitable for so called "digital analysis" or "digital PCR", such as microfluidic devices including a large number or high density of small volume reaction sites (e.g., nano-volume reaction sites or reaction volumes). Accordingly, copy number variation detection and analysis techniques of the present invention can include distributing or partitioning a sample among hundreds to thousands of reaction volumes disposed in a reaction/assay platform or microfluidic device, including exemplary devices described herein.

The methods of the present invention include a pre-amplification step in which DNA (e.g., genomic DNA) from a biological sample is amplified using the polymerase chain reaction (PCR) or other quantitative amplification techniques. Exemplary biological samples include cells (including lysed cells and cell homoginates), serum, and biological fluids. While the methods herein are described generally with respect to human DNA (e.g., to determine copy number variation in the genome of a human patient), it will be recognized that the methods can be modified/applied to any sample having variations in amounts of genetic material. For example, the methods can be used for genetic analysis of animals, plants, bacteria and fungi, as well as for genetic analysis of human subjects. Methods for collecting and processing biological samples containing DNA are well known and need not be discussed here. For the assays of the invention, DNA may be isolated from cells or biological fluids, or the assay may be carried out using, for example, a cell lysate containing DNA. Thus, as used herein, "a DNA sample" can refer to DNA, especially genomic DNA, in purified, semi-purified or un purified form. As used herein, a step of "obtaining a DNA sample from a subject" refers simply to the fact that the DNA sample is the starting material for subsequent analytical steps (e.g., the preamplification step). "Obtaining a DNA sample" does not imply the act of, for example, collecting cells from a subject, or isolating DNA, but may simply be a matter of obtaining a tube containing precollected DNA.

FIG. 1 illustrates general steps for performing the methods described herein. In one illustrative embodiment the steps of the method involve providing a pre-amplification master mix comprising assay primers, a suitable buffer system, nucleotides, and DNA polymerase enzyme (such as a polymerase enzyme modified for "hot start" conditions), adding genomic DNA to the pre-amplification master mix, pre-amplifying the sequence(s) of interest and reference sequences, and assaying the preamplified sequences by digital PCR analysis (either in an endpoint assay or a real time assay), and comparing the frequency of the target sequence(s) relative to the frequency of the reference sequence. It will be recognized that FIG. 1 is provided to aid in understanding the invention, but is not intended to limit the invention.

In the initial step in FIG. 1, preamplification, a first polynucleotide amplification of a DNA sample obtained from a subject is carried out. In the preamplification step both a target polynucleotide sequence and a reference polynucleotide sequence are amplified. Methods for PCR amplification are well known and need to be described here.

In some embodiments, the target sequence is a sequence for which deletion or duplication is associated with a phenotype of interest. In some embodiments, the target sequence is a sequence for which deletion or duplication is not associated with a known phenotype of interest, but for which information about the distribution or correlation of the variation in particular populations is desired.

The reference sequence is a sequence having a known (or assumed) genomic copy number. Thus a reference sequence is one that is not likely to be amplified or deleted in a genome. It is not necessary to emperically determine the copy number of the reference sequence in each assay. Rather, the copy number may be assumed based on the normal copy number in the organism of interest. For example, one useful reference sequence in the human genome is the sequence of the RNaseP gene, a single-copy gene present in two copies per diploid genome (and having a copy number of 1 per haploid genome). For illustration, other useful reference sequences include β-actin and glyceraldehyde-3-phosphate dehydrogenase (GAPDH); however, it will be appreciated the invention is not limited to a particular reference sequence.

Pre-amplification can be performed as a PCR reaction with primers for both RNaseP (the reference gene) and the target gene of interest. Typically, reactions are performed for a limited number of thermal cycles (e.g., 5 cycles, or 10 cycles). In some embodiments, the optimal number of cycles will depend on the PCR efficiencies for the reference gene and target gene. In certain embodiments, the number of thermal cycles during a pre-amplification assay can range from about 4 to 15 thermal cycles, or about 4-10 thermal cycles. In certain embodiments the number of thermal cycles can be 3, 4, 5, 6, 7, 8, 9, 10, 11, 12, 13, 14, 15, or more than 15.

Pre-amplification reactions preferably are quantitative or proportional. That is, the relative number (ratio) of amplicons of the target and reference sequences should reflect the relative number (ratio) of target and reference sequence in the genomic (or other) DNA being amplified. Methods for quantitative amplification are known in the art. See, e.g., Arya et al., 2005, Basic principles of real-time quantitative PCR, *Expert Rev Mol Diagn.* 5(2):209-19. In the case of duplicated genes, primers should be selected such that each duplicated copy of the target gene of interest is separately amplified. Thus, following selective pre-amplification and distribution of the sample into separate reaction volumes, a proportional number of amplicons corresponding to each sequence will be distributed into the reaction volumes. Because the newly generated molecules of both genes reflect the original ratio, a subsequent copy number analysis can quantitate the number of molecules of the target gene and the reference gene. As a result, the ratio of the two genes can be measured accurately. Because the copy number of the reference sequence is known, the copy number of the sequence of interest can be determined.

It is desirable that the amplification efficiencies target and reference sequences be similar or approximately equal, in order not to introduce any bias in the ratio of the two gene copy numbers. For this reason, primer pairs and amplification conditions should be selected to obtain this result. The amplification efficiency of any pair of primers can be easily determined using routine techniques (see e.g., Furtado et al., "Application of real-time quantitative PCR in the analysis of gene expression." DNA amplification: Current Technologies and Applications. Wymondham, Norfolk, UK: Horizon Bioscience p. 131-145 (2004))

Although it is desirable that the amplification efficiencies target and reference sequences be approximately equal, the limited number of preamplification thermal cycles (typically less than 15, usually 10 or less than 10, most often about 5) greatly mitigates any differences in efficiency, such that the usual differences are likely to have an insignificant effect on our results.

As noted, amplification methods are known in the art. For illustration, the reaction mixture used for the pre amplification method (pre-amplification composition or mix) typically contains an appropriate buffer, a source of magnesium ions (Mg2+) in the range of about 1 to about 10 mM, preferably in the range of about 2 to about 8 mM, nucleotides, and optionally, detergents, and stabilizers. An example of one suitable buffer is TRIS buffer at a concentration of about 5 mM to about 85 mM, with a concentration of 10 mM to 30 mM preferred. In one embodiment, the TRIS buffer concentration is 20 mM in the reaction mix double strength (2x) form. The reaction mix can have a pH range of from about 7.5 to about 9.0, with a pH range of about 8.0 to about 8.5 as typical. Concentration of nucleotides can be in the range of about 25 mM to about 1000 mM, typically in the range of about 100 mM to about 800 mM. Examples of dNTP concentrations are 100, 200, 300, 400, 500, 600, 700, and 800 mM. Detergents such as Tween™ 20, Triton® X 100, and Nonidet™ P40 may also be included in the reaction mixture. Stabilizing agents such as dithiothreitol (DTT, Cleland's reagent) or mercaptoethanol may also be included. The pre-amplification reaction mix will contain primers for the pre-amplification reaction. The primers are generally the same sequence as those to be used in the subsequent PCR assays for which the sample is being prepared although generally in reduced concentration. The primer concentration can be greater, equal to, or less than the primer concentrations used in the PCR assay. Embodiments include the use of primers that are about 50, 25, 20, 10 or 5 times greater, equal to, or 10, 20, 35, 50, 65, 75, 100, 125, 150, 175, and 200 times less than that of the primer concentration in the PCR assay. Primers used in the pre-amplification can include random primers, poly A tails, and specific primers designed for the PCR assay of interest.

The reaction mix can optionally contain a reference dye for normalizing subsequent real quantitative PCR analysis results. An example of a common commercially available reference dye is ROX. A commercially available reaction mix containing ROX dye is CellsDirect 2x Reaction Mix, Cat. Nos. 11754-100 and 11754-500, available from Invitrogen Corporation.

A DNA polymerase enzyme (e.g., a Taq polymerase) is also added to the reaction mix. In one embodiment a Taq polymerase such as Platinum® Taq DNA is a recombinant Taq DNA polymerase complexed with an antibody that inhibits polymerase activity at ambient temperatures. Full polymerase activity is restored after the denaturation step in PCR, providing a "hot start."

The pre-amplified samples prepared by the methods of the present invention are particularly suited for digital PCR analyses and for distinguishing chromosomal duplication of genes. In particular, a pre-amplified sample is assayed in a plurality of low volume PCR experiments. In digital PCR, identical (or substantially similar) assays are run on a sample of the genomic DNA. The number of individual reactions for a given genomic sample may vary from about 2 to over 1,000,000. Preferably, the number of assays performed on a sample is 100 or greater, more preferably, 200 or greater, more preferably, 300 or greater. Larger scale digital PCR can also be performed in which the number of assays performed on a sample is 500 or greater, 700 or greater, 765 or greater, 1,000 or greater, 2,500 or greater 5,000 or greater 7,500 or greater, or 10,000 or greater. The number of assays performed may also be significantly large such up to about 25,000, up to about 50,000, up to about 75,000, up to about 100,000, up to about 250,000, up to about 500,000, up to about 750,000, up to about 1,000,000, or greater than 1,000,000 assays per genomic sample. The quantity of DNA used in a digital PCR assay is generally selected such that one nucleic acid fragment or less is present in each individual digital PCR reaction.

As illustrated in FIG. 1, following the pre-amplification step, the sample (or a portion thereof) comprising pre-amplification product having proportionately amplified genetic material (e.g., amplicons corresponding to target and reference polynucleotide sequences) is distributed into discrete locations or reaction volumes such that each reaction well includes, for example, an average of no more than about one amplicon per volume. Thus, most reaction volumes will have no amplicon, one target sequence amplicon, or one reference sequence amplicon. Generally it is useful to dilute the preamplified sample (typically 1:10-1:20) and/or use a small portion of the amplified sample so as to adjust the concentration of amplicons so that only (on average) there are zero or one amplicons per reaction volume. Although in some cases the product of the pre-amplification step can be used without addition of further amplification reagents (e.g., polymerase), it is generally useful to add new reagents for the amplification including, optionally, different primers. Thus, the biological sample, either prior to distribution or after, can be combined with reagents selected for quantitative or nonquantitative amplification of both a target polynucleotide sequence and a reference polynucleotide 12 (Step 2).

Moreover, although the preamplification step is generally a PCR-type amplification, the second amplification (i.e., amplification of the amplicon sequences produced in the preamplification) can be carried out using any amplification method such as; for example and not limitation, *Nasba* (Compton, 1991. Nucleic Acid Sequence-based Amplification, *Nature* 350: 91-91, 1991) and the Eberwine protocol (Van Gelder et al., Amplified RNA synthesized from limited quantities of heterogeneous cDNA. *Proc Natl Acad Sci USA.* 1990).

As noted above, it will be appreciated that the quantity of DNA templates and amplicons (a function of the amount of starting genomic DNA, the number of amplification cycles, the efficiency of amplification and the size of the reaction volumes) will be adjusted to achieve the desired distribution. One of skill in the art can determine the concentration of amplicons in the pre-amplification products and calculate an appropriate amount for input. More conveniently a set of serial dilutions of the preamplification product can be tested. For example, the device shown in FIG. 3 (commercially available from Fluidigm Corp. as the BioMark 12.765 Digital Array) allows 12 dilutions to be tested simultaneously. Optionally the optimal dilution can be determined by generating a linear regression plot. For the optimal dilution the line should be straight and pass through the origin. Subsequently the concentration of the original samples can be calculated from the plot.

Following distribution, the genomic material contained within a plurality of reaction chambers can be amplified to further conduct sample assays so as to determine the number of reaction volumes in which the amplicons corresponding to the target or reference sequence were sequestered (FIG. 1, 14). The second amplification can be carried out using the same primers as used in the preamplification or different primers (e.g., a nested set).

Differential detection and analysis of the sample can be conducted so as to distinguish signal stemming from the target polynucleotide compared to the reference polynucleotide (FIG. 1, 16). For example, analysis of separate reaction sites can be used to calculate the ratio of the number of reaction volumes containing target polynucleotide sequences and the number reaction volumes containing reference polynucleotide sequences. Methods can further include detecting and analyzing genetically-related information about target sequences in the genome of a subject, including detection of genetic deletions or duplications, loss of heterozygosity, and the like, such as aneuploidy (e.g. trisomy) and numerous other genetic abnormalities. Further detail on method steps, including various differential detection and analysis techniques, is provided below.

As disclosed above, sample containing pre-amplification product or non-amplified genetic material can be distributed into discrete locations or reaction volumes of a detection and analysis platform. Distribution of the sample can be performed using a variety of techniques and devices such as, for example, flow-based distribution in microfluidic devices including a plurality of small volume reaction sites/chambers. Generally, the distribution step of the methods described herein are implemented to isolate sample material of interest, e.g., target and reference sequences into individual reaction sites for later detection and analysis.

Within each of a plurality of reaction sites or volumes, one or more amplification assays can be conducted, including multiplex reactions detection quantitative analysis/amplification of target polynucleotide sequence and a selected reference polynucleotide sequence. The ratio of detected sequences in a sample can be calculated using detection techniques such as digital PCR analysis, monitoring real-time PCR curves and/or comparing end point images of positive reaction chambers for one assay versus another assay. Alternatively, the concentration of any sequence in a DNA sample (copies/µL) can be calculated using the number of positive reaction chambers in the device that contain at least one copy of that sequence and a ratio of concentrations of target and reference sequences can be determined to calculate copy number. See copending U.S. patent application Ser. No. 12/170,414, "Method and Apparatus for Determining Copy Number Variation Using Digital PCR," which is incorporated by reference for all purposes. Also see Dube et al., 2008, "Mathematical Analysis of Copy Number Variation in a DNA Sample Using Digital PCR on a Nanofluidic Device" PLoS ONE 3(8): e2876. doi:10.1371/journal.pone.0002876, which is incorporated by reference for all purposes.

As described above, the present invention includes methods and amplification based techniques for determining copy number variation of a target polynucleotide, e.g., in a genome of a patient, and in some instances, a pre-amplification step can be performed prior to distribution of the sample in a microfluidic device for subsequent quantitative amplification and analysis. Pre-amplification may be desired, for example, where multiple copies of one target gene are closely spaced on the same chromosome, and thus the target sequences cannot be optimally partitioned from each other during quantitative analysis, e.g., as distributed in the microfluidic device. In such cases, multiple copies of the target gene may be under-counted or quantitated as one molecule rather than two. Accordingly, the total number of copies of the gene can be underestimated.

Figure 8:
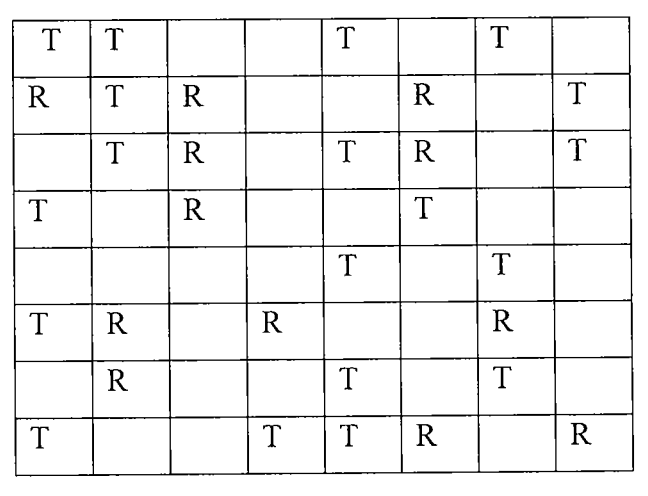

According to the present invention, CNV calculations will typically include calculation of "relative copy number" so as to advantageously distinguish apparent differences in gene copy numbers in different samples from distortion or assay noise/error, such as distortion caused by differences in sample amounts. The relative copy number of a gene (per genome) can be expressed as the ratio of the copy number of a target gene to the copy number of a single copy reference gene in a DNA sample of known concentration (copy number) in the genome of the patient, which is typically equal to 1. By using two assays for the two genes (the target polynucleotide and the reference polynucleotide) with two different labels (e.g., fluorescent dyes) on the same digital array, the methods described herein can be used to simultaneously quantitate both genes in the same DNA sample. Alternatively, and less conveniently, the target amplicons (from preamplification) can be amplified on one chip of set of reaction volumes and the test amplicons (from preamplification) can be assayed in a different set of amplicons and the data compared. The ratio of these two genes is the relative copy number of the target polynucleotide sequence, or gene of interest, in a DNA sample. In one approach this method can be summarized as determining the number of reaction volumes in which the target polynucleotide sequence or subsequence thereof is present (A) and determining the number of reaction volumes in which the reference polynucleotide sequence or subsequence thereof is present (B), and determining that the copy number of the target polynucleotide in the genome is approximately equal to (A)/(B)×N, where N is the predetermined genomic copy number of the reference sequence. It will be understood that the (A)/(B)×N is related approximately to copy number because ploidy in most organisms are low (e.g., humans normally have two copies of somatic chromosomes) while the number of amplicons detected in the present invention is inherently subject to experimental error. For example, (A) may be experimentally determined to be 936 and (B) may be experimentally determined to be 596 and N may be 1 per haploid genome. (A)/(B)×N is equal to 1.57 (approximately 1.5) which would be understood to indicate that be approximately 1.5 copies of A per haploid genome (i.e., trisomy of A). See FIG. 8 and Example below.

A variety of detection platforms or microfluidic devices and methods can be used in the practice of the invention. In some embodiments devices can be constructed using a wide variety of materials, such as glass, plastic, silicon, elastomeric polymers (e.g., polydimethylsiloxane, polyurethane, or other polymers). In certain embodiments of the present invention, microfluidic devices used to carry out aspects of the present invention are typically constructed at least in part from elastomeric materials and constructed by single and multilayer soft lithography (MSL) techniques and/or sacrificial-layer encapsulation methods (see, e.g., Unger et al., 2000, Science 288:113-116, and PCT Publication WO 01/01025, both of which are incorporated by reference herein in their entirety for all purposes). Utilizing such methods, microfluidic devices can be designed in which solution flow through flow channels of the device is controlled, at least in part, with one or more control channels that are separated from the flow channel by an elastomeric membrane or segment. This membrane or segment can be deflected into or retracted from the flow channel with which a control channel is associated by applying an actuation force to the control channels. By controlling the degree to which the membrane is deflected into or retracted out from the flow channel, solution flow can be slowed or entirely blocked through the flow channel. Using combinations of control and flow channels of this type, one can prepare a variety of different types of valves and pumps for regulating solution flow as described in extensive detail in Unger et al., supra, PCT Publication WO 02/43615 and WO 01/01025.

Sample distribution in the microfluidic devices described herein can be implemented in-part due to certain properties of elastomeric materials, which are recognized generally in the art. For example, Allcock et al. (Contemporary Polymer Chemistry, 2nd Ed.) describes "elastomers" or "elastomeric material" in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application.

Given the tremendous diversity of polymer chemistries, precursors, synthetic methods, reaction conditions, and potential additives, a wide range of properties can be selected for certain uses and applications. Therefore, with regards to the present invention, there are a large number of possible elastomer systems that can be used to make monolithic elastomeric microvalves and pumps. Some of the microfluidic devices described herein are fabricated from an elastomeric polymer such as GE RTV 615 (formulation), a vinyl-silane crosslinked (type) silicone elastomer (family). However, the present microfluidic systems are not limited to this one formulation, type or even this family of polymer; rather, nearly any elastomeric polymer is suitable. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in Unger et al. (2000) Science 288:113-116, and PCT Publications WO 02/43615, and WO 01/01025, and which are incorporated herein by reference in their entirety for all purposes.

Device Fabrication and Thermocycling.

As indicated, techniques of the present invention can incorporate use of a wide variety of detection platforms, including high throughput microfluidic devices suitable for digital analysis or digital PCR. Aspects of device fabrication, system components, and thermocyling aspects are described in greater detail below.

In one embodiment, microfluidic devices suitable for use in the present invention can be constructed utilizing single and multilayer soft lithography (MSL) techniques and/or sacrificial-layer encapsulation methods. One basic MSL approach involves casting a series of elastomeric layers on a micro-machined mold, removing the layers from the mold and then fusing the layers together. In the sacrificial-layer encapsulation approach, patterns of photoresist are deposited wherever a channel is desired. These techniques and their use in producing microfluidic devices is discussed in detail, for example, by Unger et al. (2000) Science 288:113-116, and by Chou, et al. (2000) "Integrated Elastomer Fluidic Lab-on-a-chip-Surface Patterning and DNA Diagnostics," in Proceedings of the Solid State Actuator and Sensor Workshop, Hilton Head, S.C.; and in PCT Publication WO 01/01025, each of which is incorporated herein by reference in their entirety for all purposes.

In brief, the foregoing exemplary fabrication methods initially involve fabricating mother molds for top layers (e.g., the elastomeric layer with the control channels) and bottom layers (e.g., the elastomeric layer with the flow channels) on silicon wafers by photolithography with photoresist (Shipley SJR 5740). Channel heights can be controlled precisely by the spin coating rate. Photoresist channels are formed by exposing the photoresist to UV light followed by development. Heat reflow process and protection treatment is typically achieved as described by M. A. Unger, H.-P. Chou, T. Throsen, A. Scherer and S. R. Quake, Science (2000) 288: 113, which is incorporated herein by reference in its entirety. A mixed two-part-silicone elastomer (GE RTV 615) is then spun into the bottom mold and poured onto the top mold, respectively. Spin coating can be utilized to control the thickness of bottom polymeric fluid layer. The partially cured top layer is peeled off from its mold after baking in the oven at 80° C. for 25 minutes, aligned and assembled with the bottom layer. A 1.5-hour final bake at 80° C. is used to bind these two layers irreversibly. Once peeled off from the bottom silicon mother mold, this RTV device is typically treated with HCL (0.1N, 30 min at 80° C.). This treatment acts to cleave some of the Si—O—Si bonds, thereby exposing hydroxy groups that make the channels more hydrophilic.

The device can then optionally be hermetically sealed to a support. The support can be manufactured of essentially any material, although the surface should be flat to ensure a good seal, as the seal formed is primarily due to adhesive forces. Examples of suitable supports include glass, plastics and the like.

The devices formed according to the foregoing method result in the substrate (e.g., glass slide) forming one wall of the flow channel. Alternatively, the device once removed from the mother mold is sealed to a thin elastomeric membrane such that the flow channel is totally enclosed in elastomeric material. The resulting elastomeric device can then optionally be joined to a substrate support.

Layer Formation

In one embodiment, microfluidic devices, including those in which reagents are deposited at the reaction sites during manufacture, are formed of three layers. The bottom layer is the layer upon which reagents are deposited. The bottom layer can be formed from various elastomeric materials as described in the references cited above on MLS methods. Typically, the material is polydimethylsiloxane (PDMS) elastomer. Based upon the arrangement and location of the reaction sites that is desired for the particular device, one can determine the locations on the bottom layer at which the appropriate reagents should be spotted. Because PDMS is hydrophobic, the deposited aqueous spot shrinks to form a very small spot. The optionally deposited reagents are deposited such that a covalent bond is not formed between the reagent and the surface of the elastomer because, as described earlier, the reagents are intended to dissolve in the sample solution once it is introduced into the reaction site.

The other two layers of the device are the layer in which the flow channels are formed and the layer in which the control and optionally guard channels are formed. These two layers are prepared according to the general methods set forth earlier in this section. The resulting two layer structure is then placed on top of the first layer onto which the reagents have been deposited. A specific example of the composition of the three layers is as follows (ration of component A to component B): first layer (sample layer) 30:1 (by weight); second layer (flow channel layer) 30:1; and third layer (control layer) 4:1. It is anticipated, however, that other compositions and ratios of the elastomeric components can be utilized as well. During this process, the reaction sites are aligned with the deposited reagents such that the reagents are positioned within the appropriate reaction site.

In accordance with the present invention, thermocycling can be performed on the microfluidic devices. In particular, thermocycling can be used to run amplification reactions that facilitate analysis of sample distributed within the reaction chambers.

A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device (e.g., within a particular temperature region or at one or more junctions in a matrix of blind channel-type microfluidic device).

Generally, the devices are placed on a thermal cycling plate to thermal cycle the device. A variety of such plates are readily available from commercial sources, including for example the ThermoHybaid Px2 (Franklin, M A), MJ Research PTC-200 (South San Francisco, Calif.), Eppendorf Part #E5331 (Westbury, N.Y.), Techne Part #205330 (Princeton, N.J.).

To ensure the accuracy of thermal cycling steps, in certain devices it is useful to incorporate sensors detecting temperature at various regions of the device. One structure for detecting temperature is a thermocouple. Such a thermocouple could be created as thin film wires patterned on the underlying substrate material, or as wires incorporated directly into the microfabricated elastomer material itself.

Various means of temperature detection/monitoring can be included in a system/device of the present invention. For example, temperature can also be sensed through a change in electrical resistance. Thermo-chromatic materials are another type of structure available to detect temperature on regions of an amplification device. Another approach to detecting temperature is through the use of an infrared camera. Yet another approach to temperature detection is through the use of pyroelectric sensors. Other electrical phenomena, such as capacitance and inductance, can be exploited to detect temperature in accordance with embodiments of the present invention. Using known equations for thermal diffusivity and appropriate values for the elastomers and glass utilized in the device, one can calculate the time required for the temperature within the reaction site to reach the temperature the controller seeks to maintain.

In addition to the various potentially suitable material compositions and properties, suitable microfluidic devices for use in the present invention can include a variety of features, designs, channel architectures, and the like. Devices will typically include a plurality of "flow channels," which refer generally to a flow path through which a solution can flow. Additionally, the devices can include "control channels," or channels designed to interface with flow channels such that they may be used to actuate flow within the flow channels. Devices can further include features to further regulate fluid flow, such as a "valve," which can include a configuration in which a flow channel and a control channel intersect and are separated by an elastomeric membrane that can be deflected into or retracted from the flow channel in response to an actuation force. Also, certain embodiments may include a "via," which refers to a channel formed in an elastomeric device to provide fluid access between an external port of the device and one or more flow channels. Thus, a via can serve as a sample input or output, for example.

Figure 2A:
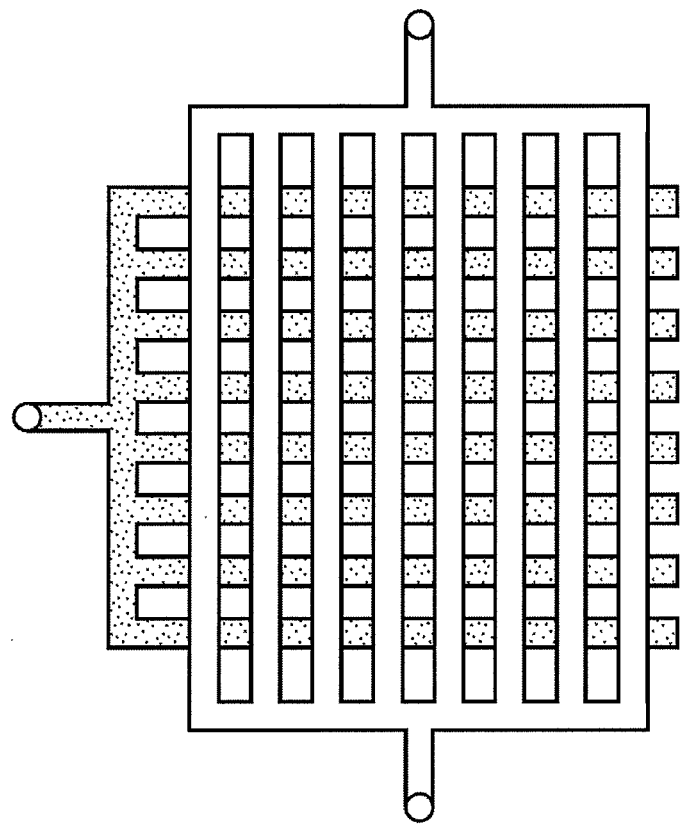
FIGS. 2A-2B illustrate exemplary channel designs of a microfluidic device, according to embodiments of the present invention.

Numerous types of channel architectures or designs can be implemented in the present invention. As illustrated in FIG. 2A, one type of channel design that can be included in a device of the present invention includes an open channel design. "Open channels" or "open-end channels" refer to a flow channel disposed between separate via, such that the flow channel has a entrance (e.g., inlet) separate from an exit (e.g., outlet). In general, an open channel network design includes at least two opposing flow channel via or inlets, which can be connected about one or a plurality of branch flow channels to form an open channel network. One or more valves formed by an adjacent/overlaying control channel can be actuated to isolate discrete regions of the branch channels to form reaction sites. Such valves provide a mechanism for switchably isolating a plurality of reaction sites. As described herein, devices can include one or more open flow channels from which one or more channels branch. One or more reaction regions or reaction sites can be disposed anywhere along a length of a flow channel. A valve formed by an overlaying flow channel can be actuated to isolate the reaction site(s) disposed along the channel, thereby providing a mechanism for switchably isolating the reaction sites. Thus, each device can include a large number of reaction sites (e.g., 10,000+) and can achieve high reaction site densities, thereby allowing a significant reduction in the size of these devices compared to traditional microfluidic devices. Open channel designs can, for example, have branch flow channels that can be addressed from more than one location/via. This design aspect may be particularly advantageous, for example, if a particular channel/branch flow channel is obstructed or blocked (e.g., due to manufacturing variation, defect, etc.), as fluid can be entered from different directions and fill a channel up to opposing sides of a particular blockage or obstruction. In contrast, a channel accessible from only a single end having a blockage may only be filled up to the point of the blockage or obstruction and, if reaction sites exist beyond the blockage, those sites can be rendered unusable.

Figure 2B:
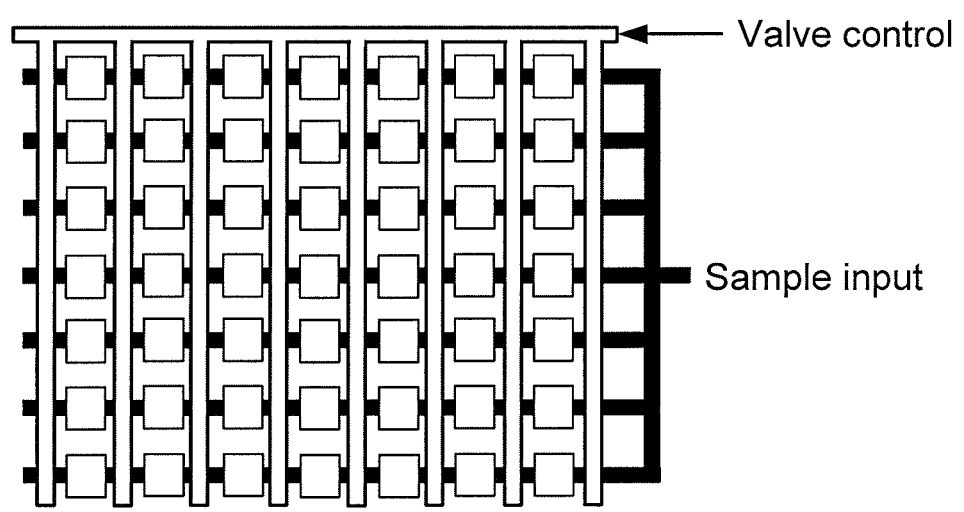

As depicted in FIG. 2B, microfluidic devices suitable for use according to the present invention may utilize a "blind channel" or "blind fill" design. Such devices are characterized in part by having one or more blind channels, or flow channels having a dead end or isolated end such that solution can only enter and exit the blind channel at one end (i.e., there is not a separate inlet and outlet for the blind channel). These devices require only a single valve for each blind channel to isolate a region of the blind channel to form an isolated reaction site. During manufacture of this type of device, one or more reagents for conducting an analysis can optionally be deposited at the reaction sites, thereby resulting in a significant reduction in the number of input and outputs. Thus, a flow channel network in communication with the blind channels can be configured such that many reaction sites can be filled with a single or a limited number of inlets (e.g., less than 5 or less than 10). The ability to fill a blind flow channel is made possible because the devices are made from elastomeric material sufficiently porous such that air within the flow channels and blind channels can escape through these pores as solution is introduced into the channels. The lack of porosity of materials utilized in other microfluidic devices precludes use of the blind channel design because air in a blind channel has no way to escape as solution is injected.

In yet another embodiment, microfluidic devices of the present invention can further optionally include guard channels in addition to flow channels and valve or control channels. In order to reduce evaporation of sample and reagents from the elastomeric microfluidic devices that are provided herein, a plurality of guard channels can be formed in the devices. The guard channels are similar to the control channels in that typically they are formed in a layer of elastomer that overlays the flow channels and/or reaction site. Hence, like control channels, the guard channels are separated from the underlying flow channels and/or reaction sites by a membrane or segment of elastomeric material. Unlike control channels, however, the guard channels are considerably smaller in cross-sectional area. In general, a membrane with smaller area will deflect less than a membrane with larger area under the same applied pressure. The guard channels are designed to be pressurized to allow solution (typically water) to be flowed into the guard channel. Water vapor originating from the guard channel can diffuse into the pores of the elastomer adjacent a flow channel or reaction site, thus increasing the water vapor concentration adjacent the flow channel or reaction site and reducing evaporation of solution therefrom. For further discussion of guard channels disposed in microfluidic devices and suitable for use according to the present invention, see, McBride et al., U.S Patent Application Publication No. 20050252773, which is incorporated herein by reference in its entirety for all purposes.

The devices further include a plurality of reaction sites, or reaction volumes, at which reagents are allowed to react, and a device may incorporate various means (e.g., pumps and valves) to selectively isolate reaction sites. The reaction sites can be located at any of a number of different locations within the device.

Because devices can include elastomeric materials that are relatively optically transparent, reactions can be readily monitored using a variety of different detection systems at essentially any location on the microfluidic device. When MSL-type devices are used most typically detection occurs at the reaction site itself. The fact that such devices are manufactured from substantially transparent materials also means that certain detection systems can be utilized with the current devices that are not usable with traditional silicon-based microfluidic devices. Detection can be achieved using detectors that are incorporated into the device or that are separate from the device but aligned with the region of the device to be detected.

In certain embodiments of the present invention, reactions within the reaction volumes are conducted using mixes or reagents that are first mixed (e.g., mixed with sample) in solution separate from the from the chip and other system components and then introduced in solution.

Devices will typically be designed and configured to conduct temperature controlled reactions, such as thermocycling amplification reactions. Thus, a device can be configured/designed for use in temperature control reactions (e.g., thermocycling reactions) within reaction volumes. A device or portion thereof, e.g., the elastomeric device, can be fixed to a support (e.g., a glass slide). The resulting structure can then be placed on a temperature control plate, for example, to control the temperature at the various reaction sites. In the case of thermocycling reactions, the device can be placed on any of a number of thermocycling plates.

As illustrated above, optional use of microfluidic devices to implement the methods of the present invention can be conducted using a wide variety of device features and designs. The following description describes in greater detail exemplary configurations that can be utilized to conduct a variety of analyses, including analyses requiring temperature control (e.g., nucleic acid amplification reactions). It should be understood, however, that these configurations are exemplary and that modifications of these systems will be apparent to those skilled in the art.

Figure 3:
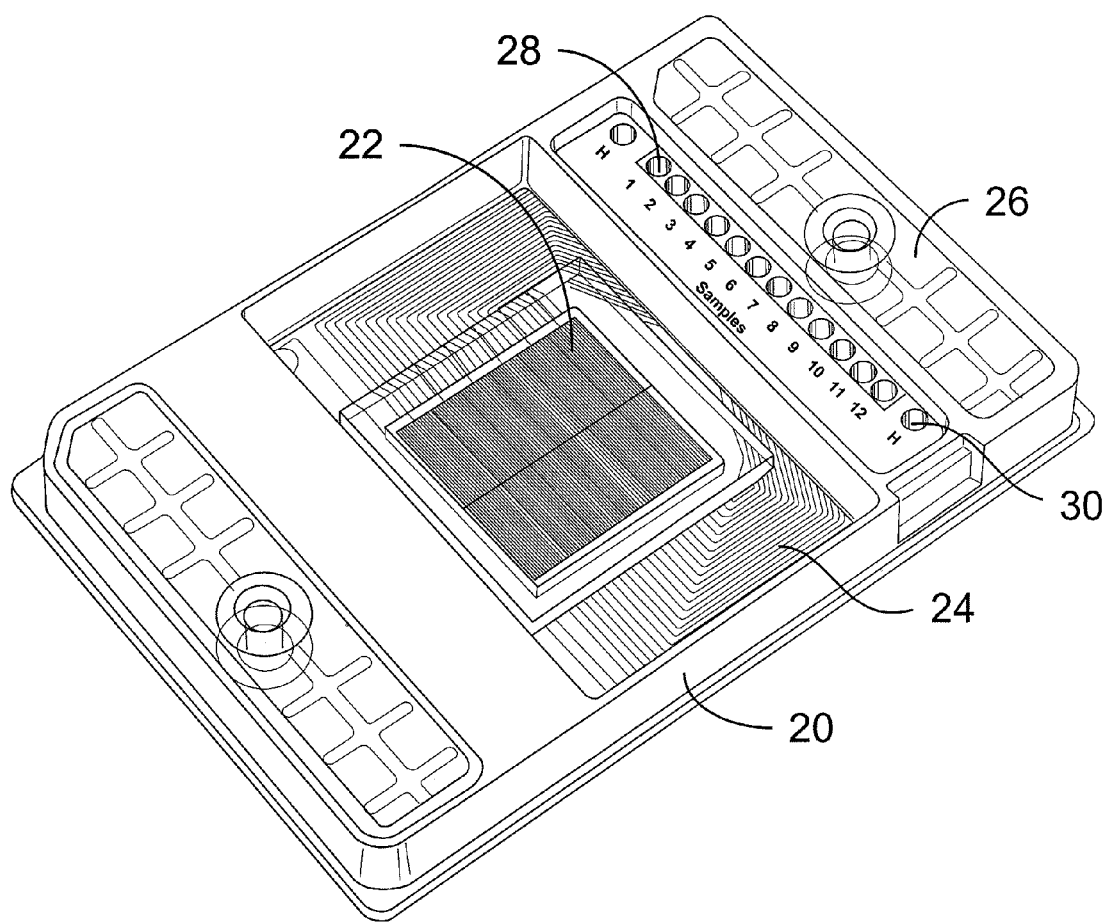
FIG. 3 is a simplified diagram of a microfluidic device, according to an embodiment of the present invention.

FIG. 3 is a simplified diagram of a microfluidic device, according to an exemplary embodiment of the present invention. As illustrated in FIG. 3, the microfluidic device, also referred to as a digital array, can include a carrier 20, which can be made from materials providing suitable mechanical support for the various elements of the microfluidic device. As an example, the device is made using an elastomeric polymer. The outer portion of the device has the same footprint as a standard 384-well microplate and enables standalone valve operation. As described below, there are 12 input ports corresponding to 12 separate sample inputs to the device. The device can have 12 panels 22 and each of the 12 panels can contain 765 6 nL reaction chambers with a total volume of 4.59 µL per panel. Microfluidic channels 24 can connect the various reaction chambers on the panels to fluid sources as described more fully below.

Pressure can be applied to an accumulator 26 in order to open and close valves connecting the reaction chambers to fluid sources. As illustrated in FIG. 3, 12 inlets 28 can be provided for loading of the sample reagent mixture. 48 inlets 28 are used in some applications to provide a source for reagents, which are supplied to the biochip when pressure is applied to accumulator 26. In applications in which reagents are not utilized, inlets 28 and reagent side accumulator 26 may not be used. Additionally, two inlets 30 are provided in the exemplary embodiment illustrated in FIG. 3 to provide hydration to the biochip. Hydration inlets 30 are in fluid communication with the device to facilitate the control of humidity associated with the reaction chambers. As will be understood to one of skill in the art, some elastomeric materials utilized in the fabrication of the device are gas permeable, allowing evaporated gases or vapor from the reaction chambers to pass through the elastomeric material into the surrounding atmosphere. In a particular embodiment, fluid lines located at peripheral portions of the device provide a shield of hydration liquid, for example, a buffer or master mix, at peripheral portions of the biochip surrounding the panels of reaction chambers, thus reducing or preventing evaporation of liquids present in the reaction chambers. Thus, humidity at peripheral portions of the device can be increased by adding a volatile liquid, for example water, to hydration inlets 30. In a specific embodiment, a first inlet is in fluid communication with the hydration fluid lines surrounding the panels on a first side of the biochip and the second inlet is in fluid communication with the hydration fluid lines surrounding the panels on the other side of the biochip.

While the devices and sample distribution described above is one exemplary system for carrying out the methods of the present invention, one of ordinary skill in the art would recognize many variations, modifications, and alternatives to designing the microfluidic devices described herein. For example, although the microfluidic device illustrated in FIG. 3 includes 12 panels, each having 765 reaction chambers with a volume of 6 nL per reaction chamber, this is not required by the present invention. The particular geometry of the digital array will depend on the particular applications. Thus, e.g., the scope of the present invention is not limited to digital arrays with 12 panels having 765 reaction chambers, but other combinations are included within the scope of the present invention. Additional description related to digital arrays suitable for use in embodiments of the present invention are provided in U.S. Patent Application Publication No. 2005/0252773, incorporated herein by reference.

Running large numbers of replicate samples can require significant quantities of reagents. In an embodiment of the present invention, digital PCR is conducted in microvolumes. The reaction chambers for running low volume PCR may be from about 2 nL to about 500 nL. The lower the reaction chamber volume, the more the number of individual assays that may be run (either using different probe and primer sets or as replicates of the same probe and primer sets or any permutation of numbers of replicates and numbers of different assays). In one embodiment, the reaction chamber is from about 2 nL to about 50 nL, preferably 2 nL to about 25 nL, more preferably from about 4 nL to about 15 nL. In some embodiments, the reaction chamber volume is about 4 nL, about 5 nL, about 6, nL, about 7 nL, about 8, nL, about 9 nL, about 10 nL, about 11 nL, or about 12, nL. The sample chambers may be constructed of glass, plastic, silicon, elastomeric polymers such as polydimethylsiloxane, polyurethane, or other polymers. The samples processed by the method of the invention are well suited for use in variable copy number analysis using the BioMark™ system (Fluidigm Corporation, South San Francisco, Calif.). The BioMark™ system uses a polydimethylsiloxane microfluidic device that provides for running multiple assays on multiple samples.

The Fluidigm microfluidic devices (digital arrays) are manufactured by Fluidigm Corporation (South San Francisco, Calif.). Chips are fabricated following the Multilayer Soft Lithography (MSL) methodology (Unger M A, Chou H P, Thorsen T, Scherer A, Quake S R, Monolithic microfabricated valves and pumps by multilayer soft lithography, Science 2000; 288:113-116). The chip has sample channels that have 10 µm average semi-elliptical depth, 70 µm width, with parallel spacing 200 µm on-center. Sample fluidics are fabricated with a two-layer mold process to create partition chambers 265 µm (depth)×150 µm×150 µm arranged along each sample channel. On a separate silicone layer, the control channels of the chip run perpendicular to the sample channels. The intersections of the channels form deflective valves for routing fluids. Upon pressurization of the control channels, a thin membrane between layers closes off the sample channels to isolate individual partition chambers. The control channels are 15 µm deep, 50 µm wide with parallel spacing 300 µm on center.

Reaction mixes, such as PCR mixes, sample mixes, pre-amplification product sample mixes, are loaded into each panel and single DNA molecules are randomly partitioned into the various reaction chambers. After loading of the panels and reaction chambers, the digital array can be thermocycled and then imaged on an appropriate reader, for example, a BioMark™ instrument available from the present assignee. The data produced is analyzed using Digital PCR Analysis software available from the present assignee or other suitable analysis software. Additional description of exemplary detection and/or analysis techniques suitable for use in embodiments of the present invention are provided in U.S. patent application Publication No. U.S. application Ser. No. 12/170,414 entitled "Copy Number Variation Determination by Digital PCR," which is copending and commonly assigned and hereby incorporated by reference for all purposes.

FIGS. 4A-4C are simplified diagrams of portion of the device/biochip illustrated in FIG. 3. FIG. 4A illustrates the 12 panels 22, each of the panels including a number of reaction chambers. FIG. 4B illustrates the geometry of a number of reaction chambers 40 contained in a panel. The reaction chambers 40 are spaced on 200 µm centers as illustrated. FIG. 4C illustrates a fluorescence image of a portion of a panel. The left side of the illustration is a control section, with all the reaction chambers illustrated as dark. The right side of the illustration shows how in a typical experiment, many of the reaction chambers are dark 42, generating no significant fluorescent emission. However, a portion of the reaction chambers have fluorescent emission, indicating a "positive" reaction chamber 44. As described above in FIG. 2B, sample channels run left to right connecting individual reaction chambers and control channels run top to bottom in the lower layer. Upon pressurization of the control channels, a thin membrane between layers closes off the sample channels to isolate individual reaction chambers. The valves partition individual chambers that are kept closed during the PCR experiment.

As described more fully throughout the present specification, the chip was thermocycled and imaged on the BioMark™ real-time PCR system available from the present assignee and Digital PCR Analysis software, such as the BioMark™ Digital PCR Analysis available from the present assignee, was used to count the number of positive chambers in each panel. When two assays with two fluorescent dyes are used in a multiplex digital PCR reaction, two genes can be independently quantitated. This ability to independently quantitate genes is used as described herein to study copy number variations using the digital array. The number of genes that can be independently quantitated in a single PCR reaction is dependent on the number of fluorescent dyes and filters available.

As described in the general methods steps above, following distribution of the sample additional steps include an amplification step followed by detection and analysis of results. In some embodiments of the present invention, amplification and detection/analysis can be conducted using methods that coordinate the two steps together, e.g., quantitative PCR. Generally, polynucleotides that are isolated within each reaction site can be amplified, detected and analyzed using a range of possible strategies. One exemplary strategy involves amplifying target and reference polynucleotides so that the amplified product can be used to determine a concentration of target polynucleotide and a concentration of the reference polynucleotide. To conduct the amplification, reagents necessary for amplification are combined with the sample and can include a first probe that selectively hybridizes to a target polynucleotide and a second probe that selectively hybridizes to a reference polynucleotide under conditions that are suitable for polynucleotide amplification. The first and second probes can include different detectable labels, so as to differentiate between the target and reference polynucleotide amplification products. Furthermore, differentiation of the target and reference polynucleotides can provide for further calculation of the concentration of target nucleotide molecules as a ratio of the reference nucleotide molecules so as to determine the relative copy number of the target polynucleotide sequence in the genome of the subject.

The general steps of amplification followed by detection and analysis can be performed using a number of ways.

To enhance understanding of the methods and systems described throughout the specification, terms of art are generally described below. The term "reagent" refers broadly to any agent used in a reaction. A reagent can include a single agent which itself can be monitored (e.g., a substance that is monitored as it is heated) or a mixture of two or more agents. A reagent may be living (e.g., a cell) or non-living. Exemplary reagents for a nucleic acid amplification reaction include, but are not limited to, buffer, metal ions, polymerase, primers, template nucleic acid, nucleotides, labels, dyes, nucleases and the like. Reagents for enzyme reactions include, for example, substrates, cofactors, coupling enzymes, buffer, metal ions, inhibitors and activators. Reagents for cell-based reactions include, but are not limited to, cells, cell specific dyes and ligands (e.g., agonists and antagonists) that bind to cellular receptors. Reagents can be included in the sample solution, or can optionally be immobilized in a variety of ways (e.g., covalently, non-covalently, via suitable linker molecules). In on-chip nucleic acid amplification reactions, for example, one or more reagents used in conducting extension reactions can be deposited (e.g., through spotting) at each of the reaction sites during manufacture of the device.

The term "label" refers to a molecule or an aspect of a molecule that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, enzymes linked to nucleic acid probes and enzyme substrates. The term "detectably labeled" means that an agent has been conjugated with a label or that an agent has some inherent characteristic (e.g., size, shape or color) that allows it to be detected without having to be conjugated to a separate label.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

A primer that is "perfectly complementary" has a sequence fully complementary across the entire length of the primer and has no mismatches. The primer is typically perfectly complementary to a portion (subsequence) of a target sequence. A "mismatch" refers to a site at which the nucleotide in the primer and the nucleotide in the target nucleic acid with which it is aligned are not complementary. The term "substantially complementary" when used in reference to a primer means that a primer is not perfectly complementary to its target sequence; instead, the primer is only sufficiently complementary to hybridize selectively to its respective strand at the desired primer-binding site.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

Detection occurs at a "detection section," or "detection region." These terms and other related terms refer to the portion of the microfluidic device at which detection occurs. As indicated above, with devices utilizing certain designs (e.g., open channel design, blind channel design, etc.), the detection section is generally the reaction site as isolated by the valve associated with each reaction site. The detection section for matrix-based devices is usually within regions of flow channels that are adjacent an intersection, the intersection itself, or a region that encompasses the intersection and a surrounding region.

As discussed above, exemplary copy number variation analyses can be conducted using quantitative PCR methods on-chip. In particular, quantitative PCR can involve both amplification of polynucleotides and detection/analysis of the amplified products. In addition to qPCR, a variety of so-called "real time amplification" methods or "real time quantitative PCR" methods can also be utilized to determine the quantity of a target nucleic acid present in a sample by measuring the amount of amplification product formed during or after the amplification process itself. Fluorogenic nuclease assays are one specific example of a real time quantitation method which can be used successfully with the devices described herein. This method of monitoring the formation of amplification product involves the continuous measurement of PCR product accumulation using a dual-labeled fluorogenic oligonucleotide probe—an approach frequently referred to in the literature as the "TaqMan" method.

The probe used in such assays is typically a short (e.g., about 20-25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. The probe is designed to have at least substantial sequence complementarity with the probe binding site on the target nucleic acid. Upstream and downstream PCR primers that bind to regions that flank the probe binding site are also included in the reaction mixture.

When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector.

One detector which is specifically adapted for measuring fluorescence emissions such as those created during a fluorogenic assay is the ABI 7700 manufactured by Applied Biosystems, Inc. in Foster City, Calif. Computer software provided with the instrument is capable of recording the fluorescence intensity of reporter and quencher over the course of the amplification. These recorded values can then be used to calculate the increase in normalized reporter emission intensity on a continuous basis and ultimately quantify the amount of the mRNA being amplified.

Additional details regarding the theory and operation of fluorogenic methods for making real time determinations of the concentration of amplification products are described, for example, in U.S. Pat. Nos. 5,210,015 to Gelfand, 5,538,848 to Livak, et al., and 5,863,736 to Haaland, as well as Heid, C. A., et al., *Genome Research,* 6:986-994 (1996); Gibson, U. E. M, et al., *Genome Research* 6:995-1001 (1996); Holland, P. M., et al., *Proc. Natl. Acad. Sci. USA* 88:7276-7280, (1991); and Livak, K. J., et al., *PCR Methods and Applications* 357-362 (1995), each of which is incorporated by reference in its entirety. Thus, as the amplification reaction progresses, an increasing amount of dye becomes bound and is accompanied by a concomitant increase in signal.

In performing amplification assays on-chip, multiplex amplifications can be performed within a single reaction site by, for example, utilizing a plurality of primers, each specific for a particular target nucleic acid of interest (e.g., target polynucleotide sequence and reference polynucleotide sequence), during the thermal cycling process. The presence of the different amplified products can be detected using differentially labeled probes to conduct a quantitative RT-PCR reaction or by using differentially labeled molecular beacons (see supra). In such approaches, each differentially labeled probes is designed to hybridize only to a particular amplified target. By judicious choice of the different labels that are utilized, analyses can be conducted in which the different labels are excited and/or detected at different wavelengths in a single reaction. Further guidance regarding the selection of appropriate fluorescent labels that are suitable in such approaches include: *Fluorescence Spectroscopy* (Pesce et al., Eds.) Marcel Dekker, New York, (1971); White et al., *Fluorescence Analysis: A Practical Approach*, Marcel Dekker, New York, (1970); Berlman, *Handbook of Fluorescence Spectra of Aromatic Molecules, $2^{nd}$ ed.*, Academic Press, New York, (1971); Griffiths, *Colour and Constitution of Organic Molecules*, Academic Press, New York, (1976); *Indicators* (Bishop, Ed.). Pergamon Press, Oxford, 19723; and Haugland, *Handbook of Fluorescent Probes and Research Chemicals*, Molecular Probes, Eugene (1992).

When microfluidic devices such as open channel or blind channel design devices are utilized to perform nucleic acid amplification reactions, the reagents that can be deposited within the reaction sites are those reagents necessary to perform the desired type of amplification reaction. Usually this means that some or all of the following are deposited, primers, polymerase, nucleotides, metal ions, buffer, and cofactors, for example. The sample introduced into the reaction site in such cases is the nucleic acid template. Alternatively, however, the template can be deposited and the amplification reagents flowed into the reaction sites. When the matrix device is utilized to conduct an amplification reaction, samples containing nucleic acid template can be flowed through the vertical flow channels and the amplification reagents through the horizontal flow channels or vice versa.

In general, multiple genotyping and expression analyses can be, for example, conducted at each reaction site. Sample containing the target DNA can be introduced into reaction sites on a microfluidic device. For quantitative PCR methods such as TaqMan®, primers for amplifying different regions of a target DNA of interest are included within a single reaction site. Differentially labeled probes for each region are utilized to distinguish product that is formed, e.g. target and reference polynucleotides. If the allele to which a probe is complementary is present in the target DNA, then amplification occurs, thereby resulting in a detectable signal. Based upon which of the differential signal is obtained, the identity of the nucleotide at the polymorphic site can be determined. If both signals are detected, then both alleles are present. Thermocycling during the reaction is performed as described in the temperature control section supra.

In some embodiments of the present invention, differentially labeled probes complementary to each of the allelic forms can be included as reagents, together with primers, nucleotides and polymerase. However, reactions can be conducted with only a single probe, although this can create ambiguity as to whether lack of signal is due to absence of a particular allele or simply a failed reaction. For the typical biallelic case in which two alleles are possible for a polymorphic site, two differentially labeled probes, each perfectly complementary to one of the alleles are usually included in the reagent mixture, together with amplification primers, nucleotides and polymerase.

As indicated by FIG. 4C, signal from each reaction site can be detected and further analyzed to determine information about the sample. For example, the samples processed by the methods of the invention are well suited for use in variable copy number analysis using the BioMark™ system (Fluidigm Corporation, South San Francisco, Calif.). and BioMark™ fluorescence imaging thermal cycler system. The BioMark™ system uses a polydimethylsiloxane microfluidic device that provides for running multiple assays on multiple samples.

As described more fully throughout the present specification, the chip can in some embodiments be thermocycled and imaged on the BioMark™ real-time PCR system available from the present assignee and Digital PCR Analysis software, such as the BioMark™ Digital PCR Analysis available from the present assignee, was used to count the number of positive chambers in each panel. When two assays with two fluorescent dyes are used in a multiplex digital PCR reaction, two genes can be independently quantitated. This ability to independently quantitate genes is used as described herein to study copy number variations using the digital array.

As described generally above, reaction mixes, such as PCR mixes, can be loaded into each panel and single DNA molecules can be randomly partitioned into the various reaction chambers. After loading of the panels and reaction chambers, the digital array is thermocycled and then imaged on an appropriate reader, for example, a BioMark™ instrument available from the present assignee. The data produced is analyzed using Digital PCR Analysis software available from the present assignee or other suitable analysis software.

As described above, quantitative PCR on-chip can be used to carry out certain embodiments of the present invention. Though, a number of different detection strategies can be utilized with the microfluidic devices described above. Selection of the appropriate system is informed in part on the type of device, event and/or agent being detected. The detectors can be designed to detect a number of different signal types including, but not limited to, signals from radioisotopes, fluorophores, chromophores, electron dense particles, magnetic particles, spin labels, molecules that emit chemiluminescence, electrochemically active molecules, enzymes, cofactors, enzymes linked to nucleic acid probes and enzyme substrates.

Illustrative detection methodologies include, but are not limited to, light scattering, multichannel fluorescence detection, UV and visible wavelength absorption, luminescence, differential reflectivity, and confocal laser scanning. Additional detection methods that can be used in certain application include scintillation proximity assay techniques, radiochemical detection, fluorescence polarization, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

The detection section can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by an optical detector. The optical detector can include one or more photodiodes (e.g., avalanche photodiodes), a fiber-optic light guide leading, for example, to a photomultiplier tube, a microscope, and/or a video camera (e.g., a CCD camera).

Detectors can be microfabricated within the microfluidic device, or can be a separate element. If the detector exists as a separate element and the microfluidic device includes a plurality of detection sections, detection can occur within a single detection section at any given moment. Alternatively, scanning systems can be used. For instance, certain automated systems scan the light source relative to the microfluidic device; other systems scan the emitted light over a detector, or include a multichannel detector. As a specific illustrative example, the microfluidic device can be attached to a translatable stage and scanned under a microscope objective. A signal so acquired is then routed to a processor for signal interpretation and processing. Arrays of photomultiplier tubes can also be utilized. Additionally, optical systems that have the capability of collecting signals from all the different detection sections simultaneously while determining the signal from each section can be utilized.

External detectors are usable because the devices that are provided are completely or largely manufactured of materials that are optically transparent at the wavelength being monitored. This feature enables the devices described herein to utilize a number of optical detection systems that are not possible with conventional silicon-based microfluidic devices.

In one embodiment, a detector uses a CCD camera and an optical path that provides for a large field of view and a high numerical aperture to maximize the amount of light collected from each reaction chamber. In this regard, the CCD is used as an array of photodetectors wherein each pixel or group of pixels corresponds to a reaction chamber rather than being used to produce an image of the array. Thus, the optics may be altered such that image quality is reduced or defocused to increase the depth of field of the optical system to collect more light from each reaction chamber.

A detector can include a light source for stimulating a reporter that generates a detectable signal. The type of light source utilized depends in part on the nature of the reporter being activated. Suitable light sources include, but are not limited to, lasers, laser diodes and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions).

A number of commercially-available external detectors can be utilized. Many of these are fluorescent detectors because of the ease in preparing fluorescently labeled reagents. Specific examples of detectors that are available include, but are not limited to, Applied Precision ArrayWoRx (Applied Precision, Issaquah, Wash.)).

In some embodiments FRET-based detection methods are used. Detection methods of this type involve detecting a change in fluorescence from a donor (reporter) and/or acceptor (quencher) fluorophore in a donor/acceptor fluorophore pair. The donor and acceptor fluorophore pair are selected such that the emission spectrum of the donor overlaps the excitation spectrum of the acceptor. Thus, when the pair of fluorophores are brought within sufficiently close proximity to one another, energy transfer from the donor to the acceptor can occur. This energy transfer can be detected. See U.S. Pat. No. 5,945,283 and PCT Publication WO 97/22719.

Molecular Beacons provide a particularly useful approach. With molecular beacons, a change in conformation of the probe as it hybridizes to a complementary region of the amplified product results in the formation of a detectable signal. The probe itself includes two sections: one section at the 5' end and the other section at the 3' end. These sections flank the section of the probe that anneals to the probe binding site and are complementary to one another. One end section is typically attached to a reporter dye and the other end section is usually attached to a quencher dye.

In solution, the two end sections can hybridize with each other to form a hairpin loop. In this conformation, the reporter and quencher dye are in sufficiently close proximity that fluorescence from the reporter dye is effectively quenched by the quencher dye. Hybridized probe, in contrast, results in a linearized conformation in which the extent of quenching is decreased. Thus, by monitoring emission changes for the two dyes, it is possible to indirectly monitor the formation of amplification product. Probes of this type and methods of their use is described further, for example, by Piatek, A. S., et al., Nat. Biotechnol. 16:359-63 (1998); Tyagi, S, and Kramer, F. R., Nature Biotechnology 14:303-308 (1996); and Tyagi, S. et al., Nat. Biotechnol. 16:49-53 (1998), each of which is incorporated by reference herein in their entirety for all purposes.

Other well-known amplification/detection methods (for illustration and not limitation) include *Invader* (see Neri, B. P., et al., *Advances in Nucleic Acid and Protein Analysis* 3826:117-125, 2000); Nasba (see, e.g., Compton, J. Nucleic Acid Sequence-based Amplification, *Nature* 350: 91-91, 1991); Scorpion (see Thelwell N., et al. Nucleic Acids Research, 28:3752-3761, 2000); and Capacitive DNA Detection (see, e.g., Sohn, et al., 2000, *Proc. Natl. Acad. Sci. U.S.A.* 97:10687-10690). Each of these references is incorporated herein by reference for all purposes.

As indicated above, methods of the present invention include conducting various reactions/amplification assays that require various reagents, compositions, buffers, additives, and the like. Reaction mixtures can be prepared at least partially either separate from an assay platform or microfluidic chip/device, or within reaction sites of the device itself (e.g., spotting). Certain reaction mixtures or compositions can be prepared and included as part of a kit or system. For example, a system can include a pre-amplification mixture/composition, an amplification assay composition, and a microfluidic device for performing amplification and copy number detection assays. Two or more components of the system can be assembled and provided as part of a kit or system.

Reactions conducted with the microfluidic devices disclosed herein can be conducted with various reagents, buffers, compositions, additives, and the like, which can be formulated to conduct reactions of the present invention (e.g., pre-amplification, quantitative amplification, etc.). So, for example, in the case of devices in which reagents are deposited reagents can be spotted with one or more reactants at a reaction site, for instance. In other embodiments, e.g., when on-chip spotting does not occur, reagents can be provided in mixes or reagent volumes separate from the chip or other system components. One set of additives are blocking reagents that block protein binding sites on the elastomeric substrate. A wide variety of such compounds can be utilized including a number of different proteins (e.g., gelatin and various albumin proteins, such as bovine serum albumin) and glycerol. A detergent additive can also be useful. Any of a number of different detergents can be utilized. Examples include, but are not limited to SDS and the various Triton detergents.

In the specific case of nucleic acid amplification reactions, a number of different types of reagents and/or additives can be included. One category are enhancers that promote the amplification reaction. Such additives include, but are not limited to, reagents that reduce secondary structure in the nucleic acid (e.g., betaine), and agents that reduce mispriming events (e.g., tetramethylammonium chloride).

Generally, the CNV calculation can be based on "relative copy number" so that apparent differences in gene copy numbers in different samples are not distorted by differences in sample amounts. The relative copy number of a gene (per genome) can be expressed as the ratio of the copy number of a target gene to the copy number of a single copy reference gene in a DNA sample, which is typically 1. By using two assays for the two genes (the target polynucleotide sequence and the reference polynucleotide sequence) with two different fluorescent dyes on the same device, both genes in the same DNA sample can be quantitated simultaneously. Accordingly, the ratio of the two genes is the relative copy number of the target nucleotide sequence in a DNA sample.

In one embodiment of the present invention, pre-amplification can be conducted using a reference gene such as RNaseP which is a single-copy gene that encodes the RNA moiety for the RNaseP enzyme, a ribonucleoprotein.

Running large numbers of replicate samples can require significant quantities of reagents. In an embodiment of the present invention, digital PCR is conducted in microvolumes. The reaction chambers for running low volume PCR may be from about 2 nL to about 500 nL. The lower the reaction chamber volume, the more the number of individual assays that may be run (either using different probe and primer sets or as replicates of the same probe and primer sets or any permutation of numbers of replicates and numbers of different assays). In one embodiment, the reaction chamber is from about 2 nL to about 50 nL, preferably 2 nL to about 25 nL, more preferably from about 4 nL to about 15 nL. In some embodiments, the reaction chamber volume is about 4 nL, about 5 nL, about 6, nL, about 7 nL, about 8, nL, about 9 nL, about 10 nL, about 11 nL, or about 12, nL. The sample chambers may be constructed of glass, plastic, silicon, elastomeric polymers such as polydimethylsiloxane, polyurethane, or other polymers. The samples processed by the methods of the present invention are well suited for use in variable copy number analysis using the BioMark™ system (Fluidigm Corporation, South San Francisco, Calif.). The BioMark system uses a polydimethylsiloxane microfluidic device that provides for running multiple assays on multiple samples.

Figure 5:
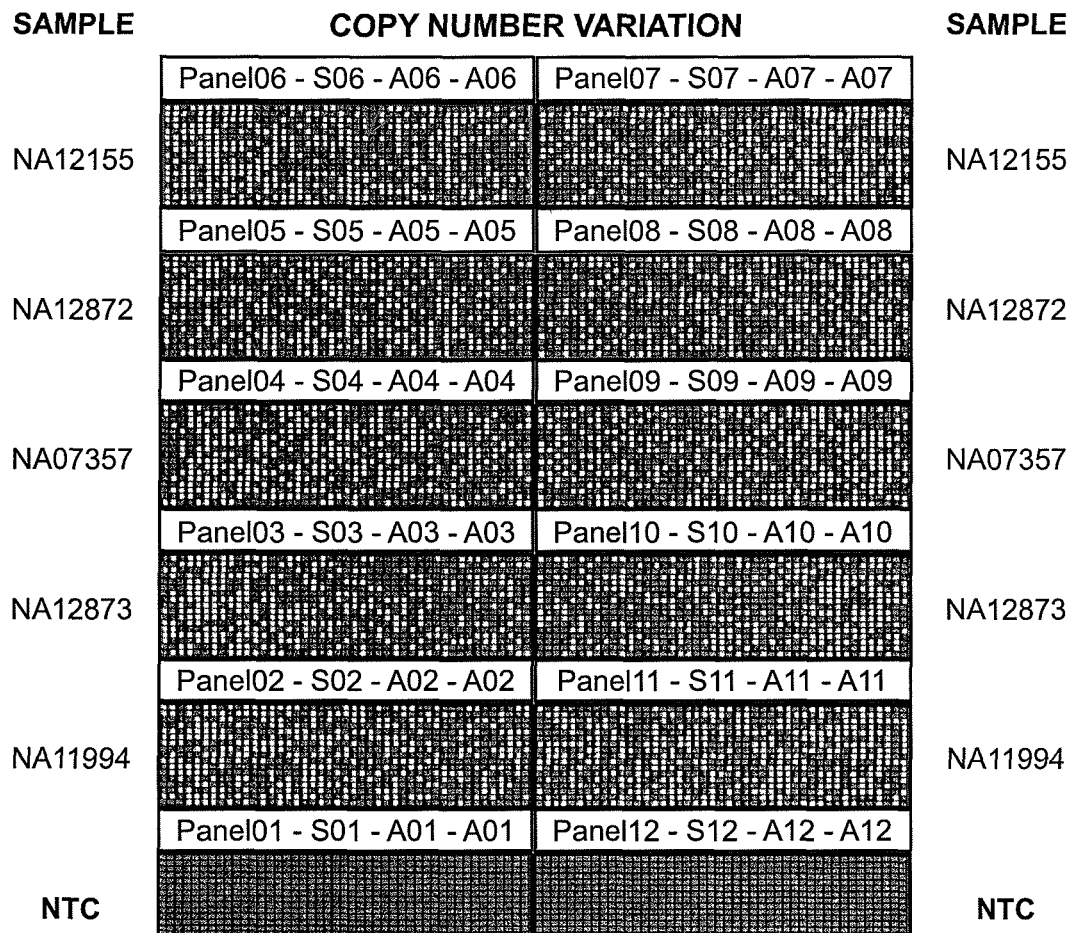
FIG. 5 illustrates exemplary copy number variation results performed using a microfluidic device.

The Fluidigm devices/nanofluidic chips (digital arrays) and BioMark fluorescence imaging thermal cycler system are manufactured by Fluidigm Corporation (South San Francisco, Calif.). An exemplary chip as illustrated in FIG. 5 has 12 panels and each of the 12 panels contains 765 6-nL chambers with a total volume of 4.59 µL per panel. Chips are fabricated following the Multilayer Soft Lithography (MSL) methodology. Unger M A, Chou H P, Thorsen T, Scherer A, Quake SR. Monolithic microfabricated valves and pumps by multilayer soft lithography. Science. 2000; 288:113-116. The chip has sample channels that have 10 µm average semi-elliptical depth, 70 µm width, with parallel spacing 200 µm on-center. Sample fluidics are fabricated with a two-layer mold process to create partition chambers 265 µm (depth)× 150 µm×150 µm arranged along each sample channel. On a separate silicone layer, the control channels of the chip run perpendicular to the sample channels. The intersections of the channels form deflective valves for routing fluids. Upon pressurization of the control channels, a thin membrane between layers closes off the sample channels to isolate individual partition chambers. The control channels are 15 µm deep, 50 µm wide with parallel spacing 300 µm on center. The outer portion has the same footprint as a standard 384-well microplate and enables stand-alone valve operation. There are 12 input ports corresponding to 12 separate sample inputs to the chip. The chips used can incorporate 765 6 nL partitioning chambers per sample input, for a total of up to 14,400 chambers per chip. In this particular embodiment, sample channels run left to right connecting individual reaction chambers and control channels run top to bottom in the lower layer. Upon pressurization of the control channels, a thin membrane between layers closes off the sample channels to isolate individual reaction chambers. The valves partition individual chambers that are kept closed during the PCR experiment.

For running real time PCR reactions, a master amplification mix (e.g., "master mix") is combined with sample including product of the pre-amplification assay. Master mixes contain an appropriate buffer, a source of magnesium ions (Mg2+) in the range of about 1 to about 10 mM, preferably in the range of about 2 to about 8 mM, nucleotides, and optionally, detergents, and stabilizers. An example of one suitable buffer is TRIS buffer at a concentration of about 5 mM to about 85 mM, with a concentration of 10 mM to 30 mM preferred. In one embodiment, the TRIS buffer concentration is 20 mM in the reaction mix double strength (2×) form. The reaction mix can have a pH range of from about 7.5 to about 9.0, with a pH range of about 8.0 to about 8.5 as typical. Concentration of nucleotides can be in the range of about 25 mM to about 1000 mM, typically in the range of about 100 mM to about 800 mM. Examples of dNTP concentrations are 100, 200, 300, 400, 500, 600, 700, and 800 mM. Detergents such as Tween™ 20, Triton® X 100, and Nonidet™ P40 may also be included in the reaction mixture. Stabilizing agents such as dithiothreitol (DTT, Cleland's reagent) or mercaptoethanol may also be included.

DO WE NEED THIS PARAGRAPH? In addition, master mixes may optionally contain dUTP as well as uracil DNA glycosylase (uracil-N-glycosylase, UNG). UNO is the product of the *Escherichia coli* ung gene, and has been cloned, sequenced and expressed in *E. coli*. Uracil-DNA-N-glycosylase (UNG) removes uracil residues from DNA (single- and double stranded) without destroying the DNA sugar-phosphodiester backbone; thus, preventing its use as a hybridization target or as a template for DNA polymerases. The resulting abasic sites are susceptible to hydrolytic cleavage at elevated temperatures. Thus, removal of uracil bases is usually accompanied by fragmentation of the DNA. Duncan, B. K., and Chambers, J. A. (1984) *GENE* 28, 211, Varshney, U., Hutcheon, T., and van de Sande, J. H. (1988) 1. *Biol. Chem.* 263, 7776. A master mix is commercially available from Applied Biosystems, Foster City, Calif., (TaqMan® Universal Master Mix, cat. nos. 4304437, 4318157, and 4326708). The use of UNG will typically be restricted to the digital PCR assay and not used in the pre-amplification assay.

For multiplex applications, different fluorescent reporter dyes are used to label separate primers or probes for quantification of different genes. For relative expression studies using multiplex PCR, the amount of primer for the reference gene (e.g., β-actin or GAPDH) should be limited to avoid competition between amplification of the reference and the sample gene. In general, the final concentration of the reference gene primer should be between 25 and 100 nM. A primer titration can be useful for optimization.

Example

In one exemplary embodiment of the present invention, the copy number of CYP2D6 was determined with and without pre-amplification. Using pre-amplification, the CYP2D6 in one sample was discovered to have a duplication (copy number was 3), whereas without pre-amplification the same sample showed a copy number of 2.

The PCR master mix useful for running PCR assays with samples prepared by the method of the invention can be prepared with the following composition: 20 mM Tris, pH 8.0, 100 mM KCl, 1% Glycerol, 0.04% Tween™, 5 mM $MgCl_2$, 400 mM dNTPs, 0.08 U/µL AmpliTaq® Gold enzyme (Applied Biosystems, Foster City, Calif.). AmpliTaq DNA Polymerase is the recombinant form of Taq DNA Polymerase. It is obtained by expressing the Taq DNA polymerase gene in an *E. coli* host. Like native TaqDNA polymerase, it lacks endonuclease and 3'-5' exonuclease activities, but has a 5'-3' exonuclease activity.

Pre-amplification in one example was performed on GeneAmp PCR system 9700 (Applied Biosystems, CA) in a 5 µL reaction containing I× PreAmp master mix (Applied Biosystems, CA), 225 nM primers (RNase P as the reference polynucleotide) and the target sequence of interest), and 1 µL of DNA sample. Thermal cycling conditions were 95° C., 10 minute hot start and 10 cycles of 95° C. for 15 seconds and 60° C. for 1 minute. 20 µL of water is added to each reaction after pre-amplification and the samples were analyzed on the digital array.

Five Coriell DNA samples were analyzed on the digital chips. The numbers of the CYP2D6 and RNase P molecules in the same volume (4.59 µL) of each sample were counted by using the BioMark Digital PCR Analysis software using the Poisson correction as well as Simant's algorithm (see Dube et al., supra.) A representative heat map is shown in simplified black and white illustration in FIG. 5. While shown as white, black, and gray events for illustration purposes, events can be recorded and graphically displayed as colors such as yellow, green, or red, corresponded to an RNase P gene (VIC, yellow), a CYP2D6 gene (FAM, red), and no gene, respectively. No template controls (NTC) were run in panels 1 and 12.

The ratios of the numbers of molecules of the CYP2D6 gene to the RNase P gene were obtained for the five samples. Two of the ratios were about 0.5, meaning there is only one copy of the CYP2D6 gene in each cell of these two samples (RNase P is a single copy gene and there are always two copies of the gene in each cell). Therefore, the individuals from which the DNA samples were collected must have a deletion of the CYP2D6 gene on one chromosome. The other three samples had a ratio of about 1, but this does not rule out the possibility of duplication since two closely linked copies will be on one molecule and can not be separated. A preamplification reaction was performed on these five samples and the preamp products were analyzed on the digital chips (Table 2).

TABLE 2

Use of pre-amplification to distinguish chromosomal duplication of genes

| SAMPLES | DIGITAL PCR CYP2D6/ RNASE P | PREAMP-DIGITAL PCR CYP2D6/ RNASE P | Copies of CYP2D6 |
|---|---|---|---|
| NA12155 | 0.49 | 0.52 | 1 |
| NA12872 | 0.97 | 0.87 | 2 |
| NA07357 | 0.85 | 0.98 | 2 |
| NA12873 | 0.49 | 0.52 | 1 |
| NA11994 | 1.06* | 1.49* | 3 |

*Sample NA11994 has duplication of the CYP2D6 gene on one chromosome

As illustrated in Table 2, two samples with a CYP2D6 to RNase P ratio of about 0.5 when genomic DNA was used still gave a ratio of about 0.5 when the preamplification process of the invention was used. A 0.5 ratio indicates a deletion. Two samples with a ratio of about 1 when genomic DNA was used also had a ratio of about 1 with preamplification products, which indicated a normal allelic status. But, one sample with a ratio of about 1 when genomic DNA was analyzed had a ratio of 1.5 when the preamplification process was used. This indicates that the sample has a duplication of the CYP2D6 gene.

Detecting Loss of Heterozygosity

One useful application of the described methods of determining copy number variation of a particular gene of interest includes detecting a loss of heterozygosity (LOH). The techniques disclosed herein can offer a new level of sensitivity and flexibility in detecting loss of heterozygosity. Exemplary applications include detection and/or study abnormal X chromosome copy number, or aneuploidy. Loss of heterozygosity (LOH) refers to a change from a heterozygous state in a normal genome to a homozygous state in a paired tumor genome. Research shows that the loss of an entire X chromosome is involved in numerous cancers. Moertel, C. A. et al., *Cancer Genet. Cytogenet.* 67:21-27 (1993). For example, 40 percent of ovarian cancers are associated with LOH for regions of the X chromosome. Osbourne, R. J. and Leech, V., *Br. J. Cancer* 69:429-438 (1994). Also, the gain of an X chromosome has been shown to be relatively common in leukemias and lymphomas. Sandberg A A. "The X chromosome in human neoplasia, including sex chromatin and congenital conditions with X-chromosome anomalies. In: Sandberg A A, editor. Cytogenetics of the mammalian X chromosome, part B: X chromosome anomalies and their clinical manifestations. New York: Alan R. Liss, 459-98 (1983).

To carry out LOH experiments, microfluidic devices as described herein can be provided. FIG. 3 shows the architecture of an exemplary device that was used for determining loss of heterozygosity in one example (see, e.g., above discussion for more device detail). Briefly, the device includes an integrated fluidic circuit (IFC) having 12 panels, each having a flow input for a sample or assay mixture. In one example, the sample was transferred to the chip for loading, and loaded by placing the digital array on the IFC controller and using the software interface to pressure load the assay components into separate panels of 765 reactions. Each of the twelve samples, which were premixed with master mix and primer-probe sets, were distributed into separate inlets on the frame of the chip. Within each panel, a single sample was partitioned into 765 individual 6 nL real-time PCR reactions. PCR was performed with the sample. The digital array was placed on a real-time PCR system for thermal cycling and fluorescence detection. The results from the experiment were viewed and analyzed using BioMark® application software. Real-time PCR curves or end point images of positive chambers were recorded to compare one assay versus another assay, e.g., the ratio of any two sequences in a DNA sample were calculated. For analysis, the digital arrays offer improved linearity, sensitivity, and ease of use.

In the described example, DNA from cell lines containing 1, 2, 3, 4 or 5 copies of the X chromosome (Coriell Institute for Medical Research, Camden, N.J.) were obtained. Digital arrays were used to test each sample against three separate X chromosome TaqMan® primer-probe sets—FAM-labeled 123B, SMS, and YY2 (BioSearch Technologies, Novato, Calif.)—which were co-amplified in the presence of a single-copy-targeting, VIC-labeled "reference" sequence.

Figure 6:
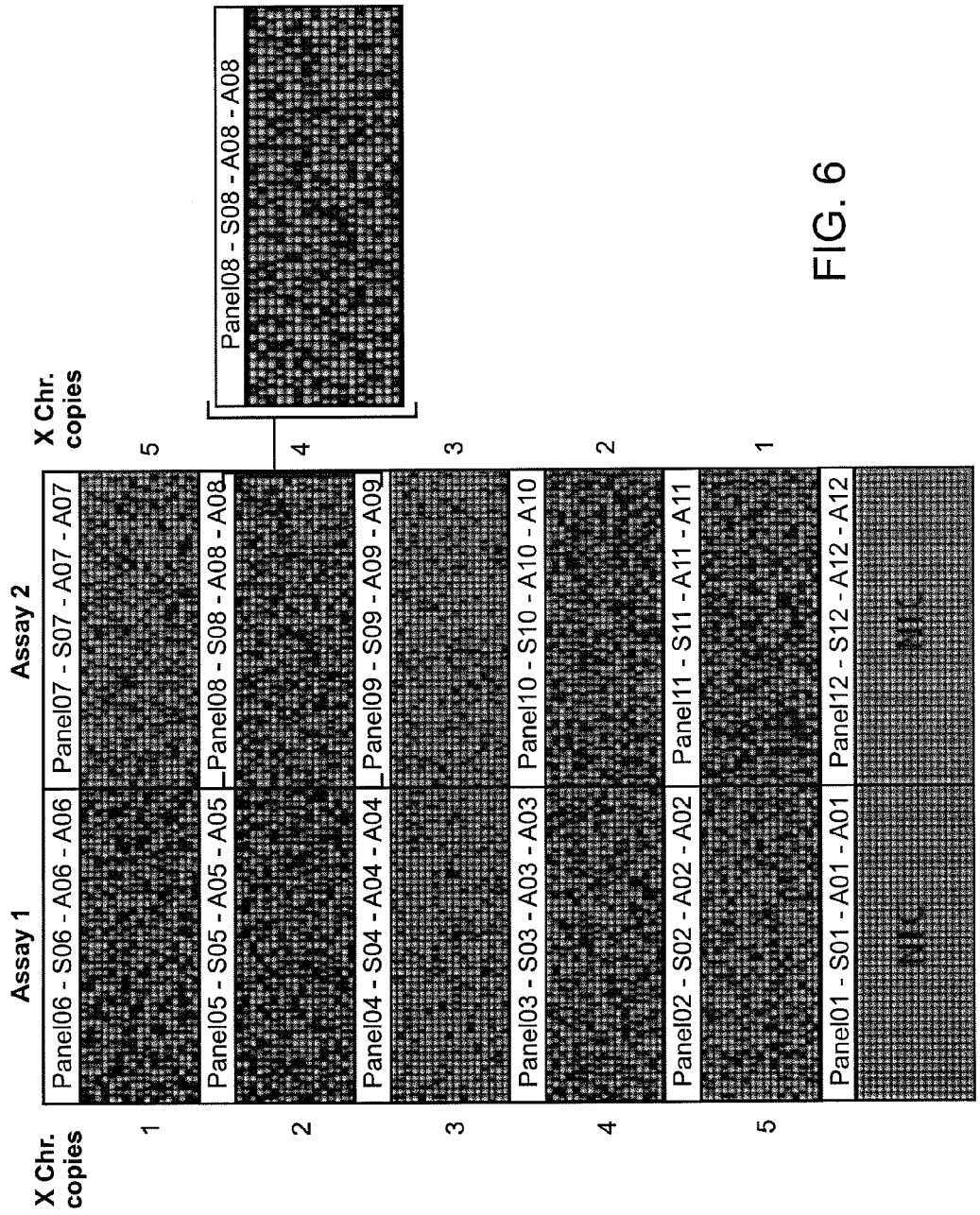
FIG. 6 illustrates exemplary loss of heterozygosity results performed using a microfluidic device.

FIG. 6 shows a black and white diagram illustrating a color-based results examining loss of heterozygosity as described, and further illustrates each test run in duplicate panels within digital arrays. FIG. 6 also shows an up-close view of Panel 4 of the device. In each panel, the number of Target positive (light gray, which correspond to one color, e.g., yellow) and Reference positive (darker gray, which correspond to a second color, e.g., red) chambers were counted and corrected for multiple dyes per chamber. From these results, the raw ratio of Target to Reference was determined. No template controls (NTC) were used in panels 1 and 12. It will be appreciated that in practice experiments can record different colors and results illustrated in color, such as red and yellow, which are depicted in FIG. 6 as grays in the black and white illustration.

Figure 7:
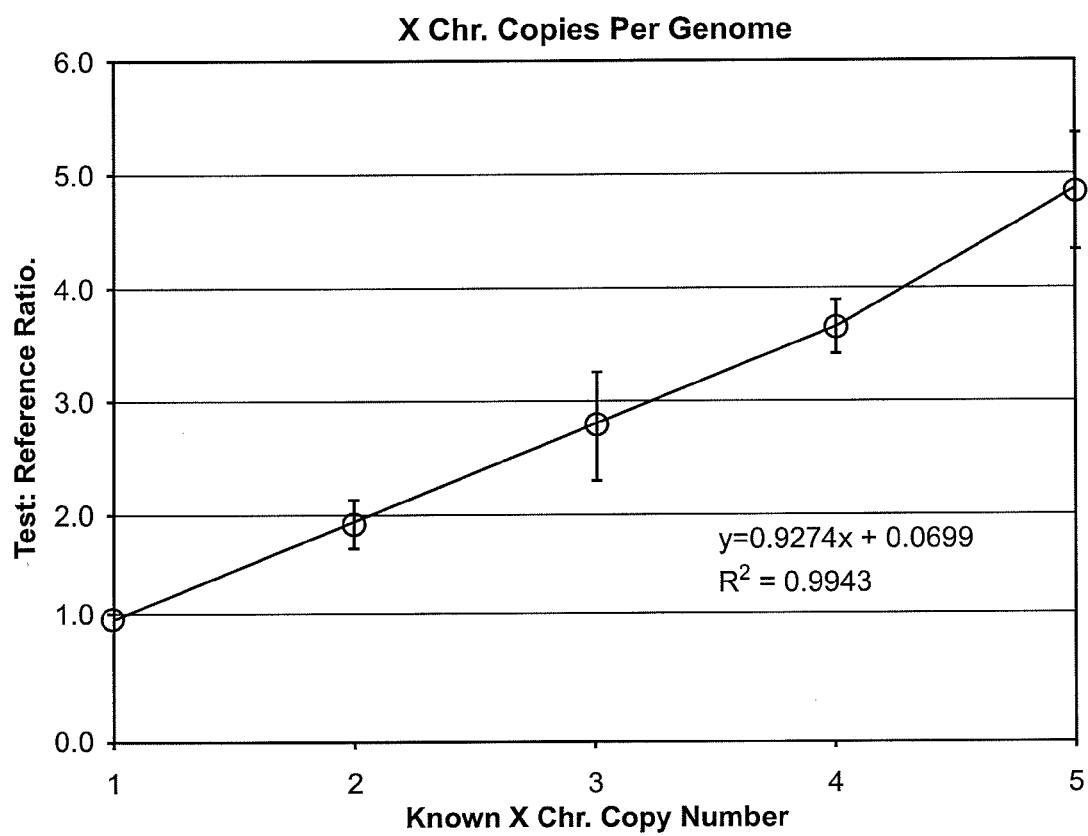
FIG. 7 is a graph depicting detection of loss of heterozygosity, according to an embodiment of the present invention.

Simple linear fitting was used to determine copy numbers. FIG. 7 shows the average of three separate assay ratios (Y-axis) plotted against known X chromosome copy number (X-axis), including error bars that show the standard error of the mean. The ratios produced slopes for DNA samples known to contain 1, 2, 3, 4 or 5 copies of the X chromosome. The individual raw ratio measurements were multiplied by 2 and averaged to obtain copy number per diploid genome. The average response for all assays, over 1-to-5 copy number variants, was an $r^2$ value of 0.994, indicating high linear assay performance.

Table 3 lists the raw ratios from the TaqMan® primer probe sets for individual X chromosome tests run on the microfluidic devices. The X chromosome mean copies per genome was determined by multiplying the mean ratio by 2. The last column on the right shows the standard error of the mean (SEM). As shown in Table 3, the mean copies per genome corresponded well with the known X chromosome copy number of a sample.

TABLE 3

Raw Ratios for Individual X Chromosome Tests

| KNOWN X CHR. COPY NUMBER | RAW FAM123 RATIO | RAW SMS RATIO | RAW YY2 RATIO | MEAN COPIES PER GENOME | SEM |
|---|---|---|---|---|---|
| 1X Chr. | 0.51 | 0.49 | 0.61 | 1.0 | 0.07 |
| 2X Chr. | 0.77 | 1.15 | 0.96 | 1.9 | 0.22 |
| 3X Chr. | 1.10 | 1.19 | 1.86 | 2.8 | 0.48 |
| 4X Chr. | 1.63 | 2.05 | 1.79 | 3.6 | 0.24 |
| 5X Chr. | 2.03 | 2.34 | 2.90 | 4.8 | 0.51 |

These results illustrate that methods and devices described herein allow detection and distinguishing of small, yet biologically relevant, differences in gene copy number within highly complex genomic DNA samples. The samples selected for these tests are similar or identical to those examined in CGH assays and MIP-based microarrays studies as described in Visakorpi et al., 1994, *Am. J. Pathol.*, 145:624-630 and Pinkel et al., 1998, Nat. Genet. 20:207-211. The present results using the methods of the current invention with digital arrays can produce copy number estimations at least as discriminating as known CGH and MIP methods while reducing hands-on technical manipulation and, therefore, requiring less labor and increased efficiency. Moreover, the ability to run multiple TaqMan® assays in a digital PCR format provides both biological robustness and assay redundancy, compensating for assay-to-assay amplification differences. If multiple loci are targeted simultaneously, overall assay results are valid even if there are single mutations or deletions at localized primer—probe binding sites. Moreover, efficacy can be enhanced by using a pre-amplification step prior to transferring the sample onto the microfluidic devices for analysis.

Although the invention has been described with reference to the above examples, it will be understood that modifications and variations are encompassed within the spirit and scope of the invention. Accordingly, the invention is limited only by the following claims along with their full scope of equivalents.

What is claimed is:

1. A method for determining the relative copy number of a target polynucleotide sequence in a genome of a subject, comprising:
   pre-amplifying a target gene sequence and a reference gene sequence in a sample containing human, non-human animal, plant, bacterial or fungal genomic DNA of the subject such that multiple copies of said target gene sequence that are linked together in the genome will be amplified separately;
   assaying the target gene sequence and the reference gene sequence of the preamplified sample by digital PCR;
   and determining a ratio of (a) to (b), where (a) is the number of amplified polynucleotide molecules containing the target gene sequence and (b) is the number of amplified polynucleotide molecules containing the reference gene sequence
   wherein the pre-amplifying comprises conducting at least 3 cycles of a polymerase chain reaction (PCR) so as to amplify the target gene sequence and reference gene sequence in substantially equal proportion.

2. The method of claim 1 wherein the target sequence is a sequence for which deletion or duplication is associated with a phenotype of interest.

3. The method of claim 1 wherein the sample is from a non-human animal, plant, bacteria or fungus.

4. The method of claim 3 wherein the sample is from a plant.

5. The method of claim 3 wherein
   i) the ratio of (a) to (b) is about 0.5 and there is a deletion of (a) on one chromosome
   ii) the ratio of (a) to (b) is about 1.5 and there is a duplication of (a) on one chromosome.

6. The method of claim 3, wherein: the reference gene sequence has a predetermined genomic copy number N; determining the number of amplified polynucleotide molecules containing the target gene sequence comprises determining the number of reaction volumes in which the target gene sequence or subsequence thereof is present (a); determining the number of amplified polynucleotide molecules containing the reference polynucleotide sequence comprises determining the number of reaction volumes in which the reference gene sequence or subsequence thereof is present (b); and the relative copy number of the target polynucleotide in the genome is approximately equal to the product of N multiplied by the ratio (a)/(b).

7. The method of claim 3, wherein pre-amplifying a target gene sequence and a reference gene sequence comprises combining the sample with a composition comprising primers specific for the target gene sequence and primers specific for reference gene sequence, and conducting a polymerase chain reaction (PCR) assay so as to separately amplify target gene sequences and reference gene sequences in substantially equal proportion.

8. The method of claim 1 wherein pre-amplifying a target gene sequence and a reference gene sequence comprises from 4 to 10 cycles.

9. The method of claim 1 wherein pre-amplifying a target gene sequence and a reference gene sequence comprises 4, 5 or 6 cycles.

10. The method of claim 1 wherein pre-amplifying a target gene sequence and a reference gene sequence comprises 7, 8 or 9 cycles.

11. The method of claim 3 wherein pre-amplifying a target gene sequence and a reference gene sequence comprises from 4 to 15 cycles.

12. The method of claim 6, wherein the reaction volumes are disposed in a microfluidic device, and the first polynucleotide amplification is conducted in a reaction volume separate from the microfluidic device.

13. The method of claim 6, wherein prior to assaying the target polynucleotide sequence and the reference polynucleotide sequence of the pre-amplified sample by digital PCR, all or a portion of the amplified sample is combined with reagents selected for quantitative amplification of target gene sequence and reference gene sequence.

14. The method of claim 13 wherein the primers used in the pre-amplification step to amplify the reference gene sequence are the same as those used in assaying the reference gene sequence of the pre-amplified sample by digital PCR.

15. The method of claim 14 wherein the primers used in the pre-amplification step to amplify the target gene sequence are the same as those used in assaying the target gene sequence of the pre-amplified sample by digital PCR.

16. The method of claim 6, wherein the reagents comprise a first probe that selectively hybridizes to a target gene sequence and a second probe that selectively hybridizes to a reference gene sequence under conditions suitable for polynucleotide amplification.

17. The method of claim 16, wherein the first and second probes comprise different detectable labels, and wherein binding of the first or second probe or degradation of the first or second probe upon polymerase chain reaction (PCR) based polymerization results in a change in detectable fluorescence of the respective detectable label.

18. The method of claim 3, wherein a ratio of target gene sequence to reference gene sequence substantially deviating from a value of 1 indicates an abnormal target gene sequence copy number in the genome.

19. The method of claim 3, wherein determining the relative copy number of the target gene sequence comprises detecting a loss of heterozygosity in the genome.

20. The method of claim 3, wherein a ratio of target gene sequence to reference gene sequence with a value substantially greater than or less than 1 indicates a loss of heterozygosity in the genome.

* * * * *